US006387366B1

(12) United States Patent
Hurwitz et al.

(10) Patent No.: US 6,387,366 B1
(45) Date of Patent: May 14, 2002

(54) METHODS FOR REDUCING ADVERSE SIDE EFFECTS ASSOCIATED WITH CELLULAR TRANSPLANTATION

(75) Inventors: David R. Hurwitz, Boston; Van Cherington, Harvard; Theofanis Galanopoulos, Arlington; Peter H. Levine, Worcester, all of MA (US); Joel S. Greenberger, Sewickley, PA (US)

(73) Assignee: ALG Company, Marlboro, MA (US)

( * ) Notice: Subject to any disclaimer, the term of this patent is extended or adjusted under 35 U.S.C. 154(b) by 0 days.

(21) Appl. No.: 09/224,048

(22) Filed: Dec. 31, 1998

(51) Int. Cl.[7] .................. A01N 63/00; A01N 43/04; A01N 65/00; C12N 5/00
(52) U.S. Cl. ................. 424/93.1; 424/93.2; 424/130.1; 424/93.21; 514/44; 435/325
(58) Field of Search .................... 435/69.1, 320.1, 435/325, 372; 424/93.21, 93.1, 93.2; 536/24.5; 514/44; 530/350, 381, 387.1

(56) References Cited

U.S. PATENT DOCUMENTS

| | | | | |
|---|---|---|---|---|
| 5,356,783 A | * | 10/1994 | Buonassisi et al. | 435/7.9 |
| 5,589,173 A | * | 12/1996 | O'Brien et al. | 424/145.1 |
| 5,726,147 A | | 3/1998 | Ruf et al. | 517/2 |
| 5,766,950 A | | 6/1998 | Greenberger et al. | 435/397 |
| 5,843,442 A | | 12/1998 | Soule et al. | 424/145.1 |
| 5,849,287 A | | 12/1998 | Greenberger et al. | 424/93.21 |

OTHER PUBLICATIONS

Plenat, F. Molecular Medicine Today. 2(6): 250–257., Jun. 1996.*

Branch, A.D. TIBS 23: 45–50, Feb. 1998.*

Majumdar, M.K. Journal of Cellular Physiology. 176:57–66, Jun. 1998.*

Miller et al. FASEB J. 9: 190–199, Feb. 1995.*

Crooke, S.T. "Basic Principles of Antisense Therapeutics", Antisense Research and Application, Springer Press, p. 1–49, 1998.*

Wilcox et al. Circulation. 82(4 Suppl 3): III48, 1990.*

Bauer et al. Thrombosis Research. 56: 425–430, 1989.*

Hurwitz et al. Human Gene Therapy. 8: 137–156, Jan. 1997.*

Cherington et al. Human Gene Therapy. 9: 1397–1407, 1990.*

Chauh et al., "Bone Marrow Stromal Cells as Targets for Gene Therapy of . . . " Human Gene Therapy 9:353–365, 1998 (Abstract Attached).

Chen et al., "Ex vivo fibroblast Transduction in Rabbits Results in Ling–term (22 600 Days) Factor . . . " Human Gene Therapy 9:2341–2351 (Abstract Attached).

Schriever et al., Tissue–factor antisense oligonucleotides. A possible tool for local . . . European Heart Journal Journal of the European Society of Cardiology, Abstract Supplement 1998.

Sudhir Agrawal, "Antisense Oligonucleotides: towards clinical trials", Oct. 1996, Tibtech, vol. 1, pp. 376–387.

K. Warzocha et al, "Antisense strategy: biological utility and prospects in the treatment of hematological malignancies", Leuk Lymphoma, vol. 24, pp. 267–281, 1997.

Bajaj et al., Tissue Factor Pathway Inhibitor: Potential Therapeutic Applications; Thrombosis and Haemostasis 78:471–477 (1997).

Bohrer et al., Role of NfkB in the Mortality of Sepsis; J. of Clinical Investigation 100:953–1324 (1997).

Roscoe O. Brady, The Sphingolipidoses; New England J. of Medicine 275:312–318 (1966).

Carey et al., Disseminated Intravascular Coagulation: Clinical and Laboratory Aspects; American Journal of Hematology 59:65–73 (1998).

Steven D. Carson, Tissue Factor (Coagulation Factor III) Inhibition by Apolipoprotein A–II; J. of Biological Chemistry 262:718–721 (1987).

Carson et al., Monoclonal Antibodies Against Bovine Tissue Factor, Which Block Interaction . . . ; Blood 66:152–156 (1985).

Conkling et al., Sphingosine Inhibits Monocyte Tissue Factor–initiated Coagulation by Altering . . .; J. of Biological Chemistry 264:18440–18444 (1989).

Dackiw et al., Prevention of Endotoxin–Induced Mortality by Antitissue Factor Immunization; Archives of Surgery 131:1273–1279 (1996).

Emami et al., Enhanced Growth of Canine Bone Marrow Stromal Cell Cultures in the Presence . . . ; In Vitro Cell Dev. Biol.—Animal 33:503–511 (1997).

(List continued on next page.)

*Primary Examiner*—Scott D. Priebe
*Assistant Examiner*—Eleanor Sorbello
(74) *Attorney, Agent, or Firm*—Synnestvedt & Lechner LLP

(57) ABSTRACT

The methods of the present invention are based on the discovery that adverse side effects (such as hemorrhage) can occur upon infusion of cells that express tissue factor. Accordingly, the methods of the invention are aimed at reducing the biological activity of tissue factor (TF) in a patient, and can be carried out by, for example: infusing fewer cells (or infuse the same number of BMSCs over a longer period of time); reducing the expression or activity of TF (within the infused cells specifically (e.g., by contacting the cells with a TF antagonist in vitro) or within the patient generally (e.g., by administering a TF antagonist to the patient); hampering the interaction of TF with factor VII(a); inhibiting the activity of the TF-factor VII(a) complex once it has formed; or inhibiting the coagulation cascade at any point downstream from formation of the complex (including inhibition of platelet activation).

12 Claims, 8 Drawing Sheets

OTHER PUBLICATIONS

Hurwitz et al., Systemic Delivery of Human Growth Hormone or Human Factor IX in Dogs by Reintroduced . . . ; Human Gene Therapy 8:137–156 (1997).

Lormeau et al., Antithrombin–mediated Inhibition of Factor VIIa–Tissue Factor complex by the Synthetic . . . ; Thrombosis and Haemostasis 76:5–8 (1996).

Majumdar et al., Phenotypic and Functional Comparison of Cultures of Marrow–Derived Mesenchymal . . . ; Journal of Cellular Physiology 176:57–66 (1998).

Orning et al., A Peptide Sequence from the EGF–2 Like Domain of FVII Inhibits . . . ; Thrombosis Research 86:57–67 (1997).

Petersen et al., Inhibitory Properties of a Novel Human Kunitz–Type Protease Inhibitor . . . ; Biochemistry 35:266–272 (1996).

Darwin J. Prockop, Marrow Stromal Cells as Stem Cells for Nonheamatopoietic Tissues; Science 276: 71–74 (1997).

Ronning et al., Synthetic Peptide Analogs of Tissue Factor and Factor VII Which Inhibit Factor . . . ; Thrombosis Research 84:73–81 (1996).

Sarver et al., Ribozymes as Potential Anti–HIV–1 Therapeutic Agents; Science 247:1222–1225 (1990).

Stephens et al., Suppression of Human Monocyte Tissue Factor Synthesis by AntiSense Oligodeoxynucleotide; Thrombosis Research 85:387–398 (1997).

Verstraete et al., Novel Antithrombotic Drugs in Development; Drugs 49:857–884 (1995).*

Warr et al., Disseminated Intravascular Coagulation in Rabbits Induced by Administration of . . . ; Blood 75:1481–1489 (1990).*

Wildgoose, P. et al., The Role of Phospholipids and the Factor VII Gla–Domain in the Interaction . . . ; Thrombosis and Haemostasis 67:679–685 (1992).*

Zhang et al., Intravenous Somatic Gene Transfer with Antisense Tissue Factor Restores Blood Flow . . . ; J. of Clinical investigation 97:2213–2224 (1996).*

* cited by examiner

```
                                                                       CCGCG     5
CCCCTCCCGCCGACACCCGCTGCCCCGCGGCGCTCCAGCCCGACCTCCGCAGGCCTCGGGGCGCGACGCCGTCCT     80
GCCAGCGAGCGAGCGAGCGCCCGCCGGGCCATGAAGACCCGCGCCCGCCCCCGGGGGCCGCGCGCCGAGGCTGCC    155
                                Met Lys Thr Arg Ala Arg Pro Arg Gly Pro Arg Ala Glu Ala Ala
GCCGCTCGGCTGCTCCTGCTCGCCTGGGCCCTCCTGCAGGTGGCCGGGGCCTCAGGCACTGCAGATGTAGTCGTA    230
Ala Ala Arg Leu Leu Leu Leu Ala Trp Ala Leu Leu Gln Val Ala Gly Ala Ser Gly Thr Ala Asp Val Val Val
GCATATAATTTAACTTGGAAATCAACTAATTTCAAGACAATTTTGGAGTGGGAACCCAAACCCATCAATCATGTC    305
Ala Tyr Asn Leu Thr Trp Lys Ser Thr Asn Phe Lys Thr Ile Leu Glu Trp Glu Pro Lys Pro Ile Asn His Val
TACACTGTTCAGATAAGCCCTAGACTAGGAAATTGGAAAAGCAAATGCTTCTACACCACAGACACGGAGTGTGAC    380
Tyr Thr Val Gln Ile Ser Pro Arg Leu Gly Asn Trp Lys Ser Lys Cys Phe Tyr Thr Thr Asp Thr Glu Cys Asp
CTCACCGATGAAATTGTGAATGACGTGCATCAGACATACCAGGCACGGGTCTTTTCCTACCCAGCTGATGCCACT    455
Leu Thr Asp Glu Ile Val Asn Asp Val His Gln Thr Tyr Gln Ala Arg Val Phe Ser Tyr Pro Ala Asp Ala Thr
GACTACTCTGGGGAGCCTCCATTTACAAACTCCCCAGAGTTCATACCTTACATAGAGACAAAGCTTGGACAGCCA    530
Asp Tyr Ser Gly Glu Pro Pro Phe Thr Asn Ser Pro Glu Phe Ile Pro Tyr Ile Glu Thr Lys Leu Gly Gln Pro
ACAATTCAGAGTTTCAAACAAGTTGGCACAGAACTGAATGTGATCGTACAAGATGCACGCACTTTGGTCAAGGTG    605
Thr Ile Gln Ser Phe Lys Gln Val Gly Thr Glu Leu Asn Val Ile Val Gln Asp Ala Arg Thr Leu Val Lys Val
AACGGCACATTTCTAAGCCTCCGGGATGTTTTCGGCAAGGACTTAAGTTACACACTTTATTACTGGAAAGCTTCA    680
Asn Gly Thr Phe Leu Ser Leu Arg Asp Val Phe Gly Lys Asp Leu Ser Tyr Thr Leu Tyr Tyr Trp Lys Ala Ser
AGTACAGGAAAGAAAACAGCCAAGACAAACACTAATGAGTTTTTGATTGATGTGGATGAAGGACAAAACTACTGT    755
Ser Thr Gly Lys Lys Thr Ala Lys Thr Asn Thr Asn Glu Phe Leu Ile Asp Val Asp Glu Gly Gln Asn Tyr Cys
TTCAGTGTTCAAGCAGGGATTCCATCACGGAAAGCTAACCAAAAGAGTCCAGAAAGTCCCATTGAGTGCACCAGC    830
Phe Ser Val Gln Ala Gly Ile Pro Ser Arg Lys Ala Asn Gln Lys Ser Pro Glu Ser Pro Ile Glu Cys Thr Ser
CACGAGAAAGGTATGTTCAGAGAAATGTTCCTCGTCATTGGAATTGTGGTGCTCGTGGTCATCATCTTCACCATC    905
His Glu Lys Gly Met Phe Arg Glu Met Phe Leu Val Ile Gly Ile Val Val Leu Val Val Ile Ile Phe Thr Ile
ATCCTGTCTGTGTCTCTGTACAAGTGCAGGAAGGTGCGAGCAAGGCAAAGCGGGAAGGAGAGCACCCCACTCAAT    980
Ile Leu Ser Val Ser Leu Tyr Lys Cys Arg Lys Val Arg Ala Arg Gln Ser Gly Lys Glu Ser Thr Pro Leu Asn
GCTGCATAAAGAAGGTGCCCTTGGAGCTGCCAACTGCGACAAAGTTTATGTTGCACTGTGACCAAGAACTTTTTA   1055
Ala Ala   (SEQ ID NO:2)
GAGAATAGAATATATAGAAACACAAATGAGTATTTTGGAGCCCGGAGACAGCTTGGGCTCACAGAAAGCTCTTTA   1130
TGGGACCTGTTCTCATGATTAGCATTCTGGTTTCGGCAGCAGCATTAGACACTTTGGAATGTAATGAACGTACAA   1205
CCCAGTCCAAGTTTTTAAAATTTCTATTTTAACACTATGGTACTTTTTGCACATACCATGTTTTAGAATGTATAT   1280
TCTGCACCCCAAATGAAACCAGGTTGTCTAATCAAAAACAAATGAACAAAAGGTTTAAGAAATCCTGGGTAGGTG   1355
TTTGGAAAACTTTTGAGGTGACTTCAAATCATGTGGGAGAGTAAAATGGAAATTGGGTGGACTCTTCTAACATAT   1430
AACATTGTTTTGTGATATATGGTATTTAGCTTCTTCTTTTTTGAGTTCTTTTGGAGGTTCAAAACAATTGGCAAA   1505
CTTTGAATGTGTTCAATGCAGAAGACTTCTGTTTTGAGGCACATTTCCTAAAGTGCCTTACAGTTTAGCACTTTA   1580
ACTGACTCAGATGCTGTGGATTAAGCACTTGACAGCTAACTCTATTTTTATAAGACTACTATACACACCATAT    1655
AGAGGTGATGATTTACGGTACTACAAGCTTTATGGTCCATATTGTATATATTTATATAATTTTATAAAAGGTTT   1730
TATACGTGGGGATTTTCTATTTATAGAAGTAATATTGTTCTGTTTGTATATATTGAGATAATTTATTTAATATAC   1805
TTTTATATATAAATAAAGGTGACTGGGAATTGTGAAAAAAAAAAAAAAAAAAAAAAAAAAA   (SEQ ID NO:1)   1866
```

FIG. 4

CGGGCGAACCCCCTCGCACTCCCTCTGGCCGGCCCAGGGCGCCTTCAGCCCAACCTCCCC 60

AGCCCCACGGGCGCCACGGAACCCGCTCGATCTCGCCGCCAACTGGTAGACATGGAGACC 120
                                                      MetGluThr

CCTGCCTGGCCCCGGGTCCCGCGCCCCGAGACCGCCGTCGCTCGGACGCTCCTGCTCGGC 180
ProAlaTrpProArgValProArgProGluThrAlaValAlaArgThrLeuLeuLeuGly

TGGGTCTTCGCCCAGGTGGCCGGCGCTTCAGGCACTACAAATACTGTGGCAGCATATAAT 240
TrpValPheAlaGlnValAlaGlyAlaSerGlyThrThrAsnThrValAlaAlaTyrAsn

TTAACTTGGAAATCAACTAATTTCAAGACAATTTTGGAGTGGGAACCCAAACCCGTCAAT 300
LeuThrTrpLysSerThrAsnPheLysThrIleLeuGluTrpGluProLysProValAsn

CAAGTCTACACTGTTCAAATAAGCACTAAGTCAGGAGATTGGAAAAGCAAATGCTTTTAC 360
GlnValTyrThrValGlnIleSerThrLysSerGlyAspTrpLysSerLysCysPheTyr

ACAACAGACACAGAGTGTGACCTCACCGACGAGATTGTGAAGGATGTGAAGCAGACGTAC 420
ThrThrAspThrGluCysAspLeuThrAspGluIleValLysAspValLysGlnThrTyr

TTGGCACGGGTCTTCTCCTACCCGGCAGGGAATGTGGAGAGCACCGGTTCTGCTGGGGAG 480
LeuAlaArgValPheSerTyrProAlaGlyAsnValGluSerThrGlySerAlaGlyGlu

CCTCTGTATGAGAACTCCCCAGAGTTCACACCTTACCTGGAGACAAACCTCGGACAGCCA 540
ProLeuTyrGluAsnSerProGluPheThrProTyrLeuGluThrAsnLeuGlyGlnPro

ACAATTCAGAGTTTTGAACAGGTGGGAACAAAAGTGAATGTGACCGTAGAAGATGAACGG 600
ThrIleGlnSerPheGluGlnValGlyThrLysValAsnValThrValGluAspGluArg

ACTTTAGTCAGAAGGAACAACACTTTCCTAAGCCTCCGGGATGTTTTTGGCAAGGACTTA 660
ThrLeuValArgArgAsnAsnThrPheLeuSerLeuArgAspValPheGlyLysAspLeu

ATTTATACACTTTATTATTGGAAATCTTCAAGTTCAGGAAAGAAAACAGCCAAAACAAAC 720
IleTyrThrLeuTyrTyrTrpLysSerSerSerSerGlyLysLysThrAlaLysThrAsn

ACTAATGAGTTTTTGATTGATGTGGATAAAGGAGAAAACTACTGTTTCAGTGTTCAAGCA 780
ThrAsnGluPheLeuIleAspValAspLysGlyGluAsnTyrCysPheSerValGlnAla

GTGATTCCCTCCCGAACAGTTAACCGGAAGAGTACAGACAGCCCGGTAGAGTGTATGGGC 840
ValIleProSerArgThrValAsnArgLysSerThrAspSerProValGluCysMetGly

FIG. 5A

```
CAGGAGAAAGGGGAATTCAGAGAAATATTCTACATCATTGGAGCTGTGGTATTTGTGGTC   900
 GlnGluLysGlyGluPheArgGluIlePheTyrIleIleGlyAlaValValPheValVal

ATCATCCTTGTCATCATCCTGGCTATATCTCTACACAAGTGTAGAAAGGCAGGAGTGGGG   960
 IleIleLeuValIleIleLeuAlaIleSerLeuHisLysCysArgLysAlaGlyValGly

CAGAGCTGGAAGGAGAACTCCCCACTGAATGTTTCATAAAGGAAGCACTGTTGGAGCTAC  1020
 GlnSerTrpLysGluAsnSerProLeuAsnValSerter  (SEQ ID NO: 4)

TGCAAATGCTATATTGCACTGTGACCGAGAACTTTTAAGAGGATAGAATACATGGAAACG  1080

CAAATGAGTATTTCGGAGCATGAAGACCCTGGAGTTCAAAAAACTCTTGATATGACCTGT  1140

TATTACCATTAGCATTCTGGTTTTGACATCAGCATTAGTCACTTTGAAATGTAACGAATG  1200

GTACTACAACCAATTCCAAGTTTTAATTTTTAACACCATGGCACCTTTTGCACATAACAT  1260

GCTTTAGATTATATATTCCGCACTTAAGGATTAACCAGGTCGTCCAAGCAAAAACAAATG  1320

GGAAAATGTCTTAAAAAATCCTGGGTGGACTTTTGAAAAGCTTTTTTTTTTTTTTTTTT  1380

TGAGACGGAGTCTTGCTCTGTTGCCCAGGCTGGAGTGCAGTAGCACGATCTCGGCTCACT  1440

TGCACCCTCCGTCTCTCGGGTTCAAGCAATTGTCTGCCTCAGCCTCCCGAGTAGCTGGGA  1500

TTACAGGTGCGCACTACCACGCCAAGCTAATTTTTGTATTTTTAGTAGAGATGGGGTTT   1560

CACCATCTTGGCCAGGCTGGTCTTGAATTCCTGACCTCAGTGATCCACCCACCTTGGCCT  1620

CCCAAAGATGCTAGTATTATGGGCGTGAACCACCATGCCCAGCCGAAAAGCTTTTGAGGG  1680

GCTGACTTCAATCCATGTAGGAAAGTAAAATGGAAGGAAATTGGGTGCATTTCTAGGACT  1740

TTTCTAACATATGTCTATAATATAGTGTTTAGGTTCTTTTTTTTTTCAGGAATACATTTG  1800

GAAATTCAAAACAATTGGGCAAACTTTGTATTAATGTGTTAAGTGCAGGAGACATTGGTA  1860

TTCTGGGCAGCTTCCTAATATGCTTTACAATCTGCACTTTAACTGACTTAAGTGGCATTA  1920

AACATTTGAGAGCTAACTATATTTTTATAAGACTACTATACAAACTACAGAGTTTATGAT  1980
```

FIG. 5B

```
TTAAGGTACTTAAAGCTTCTATGGTTGACATTGTATATATAATTTTTTAAAAAGGTTTTT 2040

CTATATGGGGATTTTCTATTTATGTAGGTAATATTGTTCTATTTGTATATATTGAGATAA 2100

TTTATTTAATATACTTTAAATAAAGGTGACTGGGAATTGTT 2141 (SEQ ID NO:3)
```

FIG. 5C

| | | |
|---|---|---|
| Human TF Protein | METPAWPRVPRPETAVARTLLLGWVFAQVAGASGTTNTVAAYNLTWKSTN | 50 |
| Canine TF Protein | MKTRARPRGPRAEAAAARLLLLAWALLQVAGASGTADVVVAYNLTWKSTN | 50 |
| Human TF Protein | FKTILEWEPKPVNQVYTVQISTKSGDWKSKCFYTTDTECDLTDEIVKDVK | 100 |
| Canine TF Protein | FKTILEWEPKPINHVYTVQISPRLGNWKSKCFYTTDTECDLTDEIVNDVH | 100 |
| Human TF Protein | QTYLARVFSYPAGNVESTGSAGEPLYENSPEFTPYLETNLGQPTIQSFEQ | 150 |
| Canine TF Protein | QTYQARVFSYPA---DATDYSGEPPFTNSPEFIPYIETKLGQPTIQSFKQ | 147 |
| Human TF Protein | VGTKVNVTVEDERTLVRRNNTFLSLRDVFGKDLIYTLYYWKSSSSGKKTA | 200 |
| Canine TF Protein | VGTELNVIVQDARTLVKVNGTFLSLRDVFGKDLSYTLYYWKASSTGKKTA | 197 |
| Human TF Protein | KTNTNEFLIDVDKGENYCFSVQAVIPSRTVNRKSTDSPVECMGQEKGEFR | 250 |
| Canine TF Protein | KTNTNEFLIDVDEGQNYCFSVQAGIPSRKANQKSPESPIECTSHEKGMFR | 247 |
| Human TF Protein | EIFYIIGAVVFVVIILVIILAISLHKCRKAGVGQSWKENSPLNVS. (SEQ ID NO: 4) | 296 |
| Canine TF Protein | EMFLVIGIVVLVVIIFTIILSVSLYKCRKVRARQSGKESTPLNAA. (SEQ ID NO: 2) | 293 |

METHODS FOR REDUCING ADVERSE SIDE EFFECTS ASSOCIATED WITH CELLULAR TRANSPLANTATION

FIELD OF THE INVENTION

The invention relates to transplantation of cells such as bone marrow cells.

BACKGROUND OF THE INVENTION

Efforts to develop safe and effective therapies by transplanting various types of biological cells have been on the rise since the 1960s. For example, scientists began to consider organ transplantation, bone marrow transplantation, and enzyme supplementation to treat rare genetic disorders soon after the enzymatic defects in Gaucher's and Niemann-Pick disease were discovered (see, e.g., Brady, *New Engl. J. Med.* 275:312, 1966). Today, certain organs (e.g., the kidney) are transplanted with great success and bone marrow transplantation is performed with increasing frequency, particularly in the context of treating cancer. Typically, cancer patients undergo autologous bone marrow transplantation; bone marrow cells are removed from the patient, maintained in an ex vivo culture while the patient is treated with radiation or by chemotherapy, and then transplanted back into the patient where they restore the bone marrow.

To effect genetic therapies, various cell types including bone marrow stromal cells (BMSCs) can be genetically modified and transplanted into a patient to treat a wide variety of disorders (see, e.g., U.S. Pat. No. 5,849,287).

SUMMARY OF THE INVENTION

The methods of the present invention are based on the discovery that certain adverse side effects (such as blood clotting and/or hemorrhage) caused by the infusion of transplanted cells, such as BMSCs, are due to the expression of tissue factor (TF) by the infused cells. BMSCs, which are described further below, are also described as mesenchymal stem cells (see, e.g., Prockop, *Science* 276:71, 1997). Accordingly, the methods of the invention are aimed at reducing the biological activity or level of TF in a patient, and can be carried out in a variety of ways. For example, one can: infuse fewer cells, e.g., BMSCs (or infuse the same number of cells over a longer period of time); reduce the expression or activity of TF (within the infused cells, e.g., by contacting the cells with a TF antagonist in vitro, or within the patient, e.g., by administering a TF antagonist to the patient; hamper the interaction of TF with factor VII(a); inhibit the activity of the TF-factor VII(a) complex once it has formed; or inhibit the coagulation cascade at any point downstream from formation of the complex (including inhibition of platelet activation). As implied by the foregoing, the term "antagonist" encompasses compounds (i.e., biological molecules, drugs, or other therapeutic agents) that interact with (and inhibit) TF directly or indirectly (by interacting with and inhibiting molecules that specifically bind TF (such as factor VII) or that lie downstream from the formation of the TF-factor VII complex). These means for reducing the biological activity or level of TF are described in detail below.

The methods of the invention may be practiced whenever patients are treated with cellular or gene therapies that employ transplanted cells, e.g., bone marrow cells, that express TF. For example, they can be practiced with cellular or gene therapies that employ bone marrow cells such as BMSCs.

The methods of the invention employ TF antagonists. Suitable antagonists include small molecules (i.e., molecules with a molecular weight below about 500), large molecules (i.e., molecules with a molecular weight above about 500), antibodies that specifically bind to and "neutralize" TF, and nucleic acid molecules that interfere with transcription or translation of TF (e.g., antisense nucleic acid molecules and ribozymes). TF antagonists also include compounds that interfere with the ability of TF to trigger blood clotting and/or coagulation. Preferably, a neutralizing antibody used in the present methods (or any of the other types of TF antagonists described herein) will neutralize at least 50%, more preferably at least 70%, and most preferably at least 80% (e.g., 85%, 90%, or 95%) of the activity of TF in a sample (e.g., a sample of BMSCs) containing TF. Antibodies and other types of antagonists are discussed in detail below.

In one embodiment, the new methods inhibit adverse vascular effects caused by introducing cells that express TF into a patient by reducing the total load of biologically active TF associated with the cells to less than about 25,000 ng/kg of the patient's weight (e.g., less than about 10,000, less than about 5,000, or less than about 2,000 ng/kg of the patient's weight).

The adverse effects that can be inhibited include hemorrhage, thrombosis, intravascular coagulation, disseminated intravascular coagulation, platelet aggregation, a reduced platelet count, reduced levels of the clotting factors V, VIII, and IX, an increased level of thrombin-antithrombin (TAT), an increased level of fibrin monomers, and an increased level of D-dimers. Preferably, these adverse effects are prevented entirely or inhibited sufficiently to prevent adverse symptoms. Thus, the new methods described herein can confer a benefit to the patient even if they only attenuate the adverse effects.

In some instances, the TF-expressing cells will be cultured prior to implantation into the patient. The cells can be cultured under the conditions described herein or under conditions known and used in the art.

The TF-expressing cells can be introduced into the patient (e.g., by infusion or injection into a blood vessel such as an artery or a vein, or by injection into a muscle, the dermis, or the peritoneal cavity) so that they come to reside in a desired location. The bone marrow cavities and intrarticular spaces are useful locations.

The TF-expressing cells can be introduced in a physiologically compatible solution, or can be implanted in a matrix (such as a gel, collagen, or bone-forming matrix, or a matrix composed of ceramic (e.g., a calcium phosphate ceramic), glass, or hydroxyapatite)) before they are introduced into the patient. Moreover, the cells can be wild-type TF-expressing cells or genetically modified TF-expressing cells. For example, the cells can contain a DNA construct encoding a coagulation factor such as factor VIII or factor IX or any of a wide variety of other biologically active polypeptides known to those of skill in the art. See for example, U.S. Pat. No. 5,849,287.

Patients having numerous types of diseases or disorders can benefit from the methods described herein. These methods may be particularly well suited for treating patients with hemophilia, cancer (such as breast cancer), or osteogenesis imperfecta.

As described further below, adverse vascular side effects can be inhibited by contacting TF-expressing cells (in vivo or ex vivo) with an oligonucleotide that inhibits transcription of a tissue factor gene, the stability of the tissue factor RNA, or the ability of tissue factor RNA to be translated into protein. The oligonucleotide can be a ribonucleic acid or a deoxyribonucleic acid molecule. Alternatively, the TF-expressing cells can be contacted with a ribozyme that cleaves tissue factor RNA. Where the antagonist of TF is an antibody, the antibody can be one that inhibits: the activity of tissue factor; a polypeptide that specifically binds to tissue factor; or a polypeptide that is active in the biochemical cascade that is initiated by the formation of a complex between tissue factor and factor VII. More specifically, the antibody can be TF1-E2, TF1-F7, HTF1-7B8, TF8-5G9, TF8-11D12, TF9-9C3, TF8-5G9, AP-1, 5G9, PW-4, 231-7, 12D10, hVII-B101/B1, hVII-D2/D4 or hVII-DC6/3D8 (each of which is further described below).

Antibodies useful in the methods of the present invention can be a monoclonal, polyclonal, or engineered antibodies that specifically bind to TF (as described more fully below). An antibody that "specifically binds" to a particular antigen, for example, to TF or to a polypeptide that interacts with (e.g., binds to) TF in the course of blood clotting, will not substantially recognize or bind to other molecules in a sample (i.e., a sample of biological material) that contains TF.

Given that an object of the present invention is to alter the expression or activity of TF in vivo (e.g., in BMSCs infused in the course of cell or gene therapy), a pharmaceutical composition containing, for example, an isolated nucleic acid molecule that is antisense to TF (i.e., that has a sequence that is the reverse and complement of a portion of the coding strand of a TF gene), or an antibody, small molecule, or other compound that specifically binds to TF is also a feature of the invention.

A "patient" can be any animal including mammals such as humans and domesticated mammals, e.g., dogs, cats, horses, cows, sheep, and pigs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety.

The preferred methods and materials are described below in terms that are meant to illustrate, not limit, the invention. One of ordinary skill in the art would recognize methods and materials that are similar or equivalent to those described herein, and that can be used in the practice or testing of the present invention.

Other features and advantages of the invention will be apparent from the detailed description, and from the claims.

BRIEF DESCRIPTION OF THE DRAWINGS

FIG. 4 is a representation of the cDNA sequence and predicted amino acid sequence of canine TF (SEQ ID NOs:1 and 2, respectively).

FIGS. 5A to 5C are a representation of the cDNA sequence and predicted amino acid sequence of human TF (SEQ ID NOs:3 and 4, respectively).

FIG. 6 is an alignment of the canine TF protein sequence (SEQ ID NO:2) and the human TF protein sequence (SEQ ID NO:4).

DETAILED DESCRIPTION

Tissue Factor (TF; also known as thromboplastin) is a membrane-bound glycoprotein that complexes with free circulating factor VII and factor VIIa. Formation of this complex is believed to trigger a cascade of biochemical reactions that results in blood clotting or coagulation. More specifically, formation of a complex including TF and factor VIIa activates factors X and IX by proteolysis. This induces the coagulation cascade and leads to the generation of thrombin. Thrombin cleaves fibrinogen to fibrin, which leads to the formation of a clot. Thrombin also converts, and thereby activates, factor XI to factor XIa, factor VIII to factor VIIIa and factor V to factor Va. These factors, when activated, enhance the coagulation cascade. In addition, thrombin activates platelets, which initiate a series of events leading to large-scale thrombin generation. Regulation of thrombin is, in turn, influenced by the activities of antithrombin III (ATIII), TF pathway inhibitor (TFPI), thrombomodulin, activated protein C (APC), and protein S. Thus, normally healthy animals, such as humans and domesticated mammals, have very low levels of TF in their bloodstreams.

Numerous types of cells that can be transplanted express TF. In addition to bone marrow cells such as BMSCs, fibroblasts, myoblasts, mesothelial cells, keratinocytes, neuronal cells, chondrocytes, osteoblasts, adipocytes, vascular smooth muscle and vascular endothelial cells, and certain stem cells, as well as autologous tumor cells that are removed from a patient, manipulated, and then reinfused, all express TF to some degree. The new methods can be used in conjunction with transplantation of any cells that express TF and thereby introduce the TF into the patient's body, e.g., into the bloodstream.

In general, the TF-expressing cells can be treated prior to or after implantation, the patient can be treated with a TF-antagonist, e.g., by sustained-release or long-term infusion, or both treatments can be used in conjunction, i.e., the cells and patient are treated using the same or different methodologies.

Figure 1:
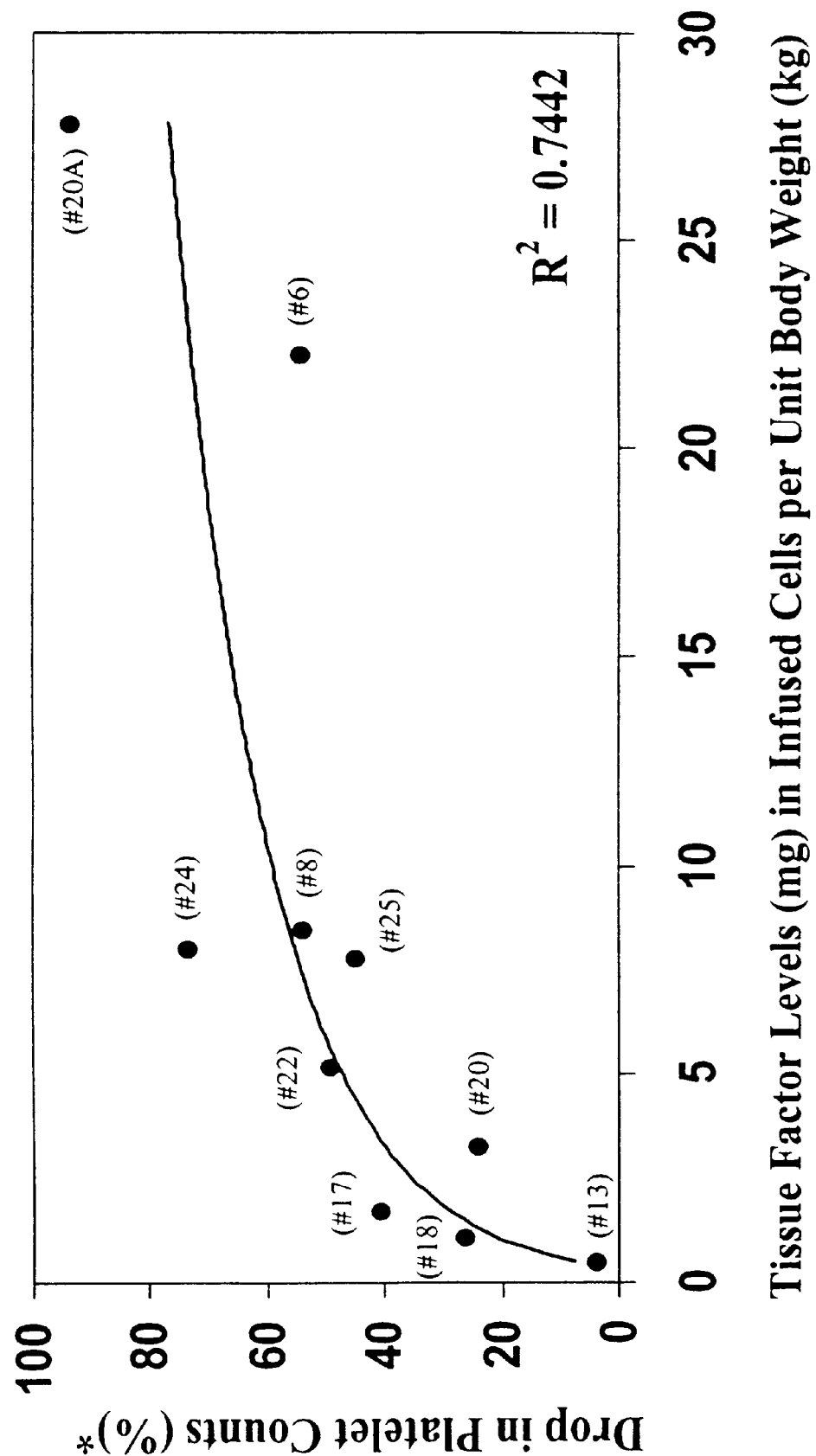
FIG. 1 is a graph depicting the correlation between the decline in platelet count (%) and the amount of TF (mg) in infused autologous BMSCs. The amount of TF is normalized to account for the weight of the animal (the numbers along the X axis represent TF (mg)/kg body weight).

A. Reducing the Biological Activity of Tissue Factor by Altering the Infusion of Cells One of the most straight-forward ways to practice the present invention is to limit the number of TF expressing cells, such as BMSCs, infused into (or otherwise administered to) a patient. The total number of cells can be limited or, alternatively, the number of cells administered at a given time can be limited. One method for determining how many cells can be transplanted without substantial risk of an adverse side effect is based on the observation that, following reinfusion of BMSCs into dogs, their platelet counts may drop below the normal level. Indeed, the analysis described below (see Example 1) revealed a correlation between the percent decline in platelet count and the level of TF within the infused autologous BMSCs. As shown in FIG. 1, the greater the level of TF in infused cells (expressed as mg TF/kg body weight), the greater the drop in platelet count (expressed as percentage drop). This drop in platelet count is caused when the platelets become involved in blood coagulation and clotting. Once a sufficient number of platelets are thus in effect removed from the circulation, hemorrhage can occur.

The measurement depicted along the X axis (TF levels in infused cells/kg body weight) was obtained by performing a TF activity assay on an aliquot of the cells infused (as described below in Example 4), extrapolating from the activity within that aliquot to the amount of TF within the total cell population infused, and dividing by the weight of the animal. Ten animals were examined, and each is represented by one of the data points shown in FIG. 1 (and labelled with an identifier, e.g., #6, #13, #20A).

The measurement depicted along the Y axis (drop in platelet count) was obtained by calculating the percent drop at one hour post-infusion (except for dog #20A, which was tested 20 minutes post-infusion).

An insignificant drop in platelet count was seen when infused cells possessed 500 ng of TF activity per kg body weight (#13). Moderate drops in platelet counts were seen when infused cells possessed 1,000–5,000 ng of TF activity per kg body weight (#18, #17, and #20). Higher drops in platelet counts were seen when infused cells possessed 5,000–25,000 ng of TF activity per kg body weight (#22, #25, #24, #8, and #6). A catastrophic drop in platelet count was seen when infused cells contained more than 25,000 ng of TF activity per kg body weight. Accordingly, one of skill in the art could prevent adverse side effects associated with transplantation of BMSCs by limiting the number of cells infused (or otherwise administered) to a number exhibiting less than 5,000 ng of TF activity per kg body weight (e.g., 4000, 3000, 2000, 1500, 1250, or 1000 ng of TF activity per kg body weight). More preferably, one could limit the number of cells infused to a number exhibiting less than 1,000 ng of TF activity per kg body weight (e.g., 800, 700, 500, 400, or 200 ng of TF activity per kg body weight).

The amount of tissue factor in a cell lysate was determined by comparing the clotting time induced in canine plasma by a cell lysate to the clotting time induced in canine plasma by a known amount (in nanograms per milliliter) of TF standard (recombinant lipidated human TF: American Diagnostica, Inc., Greenwich, Conn.).

B. Reducing the Biological Activity of Tissue Factor by Reducing Gene Expression The methods of the invention can be carried out by administering antisense TF oligonucleotides or ribozymes that inhibit the transcription of the TF gene (and thereby inhibit the biological activity of TF). Preferably, the cells expressing TF will be contacted with these oligonucleotides or ribozymes in vitro or ex vivo, before they are transplanted into a patient. Alternatively, the oligonucleotides or ribozymes can be administered to the patient so that TF expression is reduced in all of the cells within the patient that express TF, including the transplanted bone marrow cells. Preferably, an oligonucleotide or ribozyme used in the present methods will inhibit at least 50%, (e.g., 70%, 80%, 85%, 90%, or 95%) of the expression of TF in a sample (e.g., a sample of BMSCs) containing TF.

More specifically, one can utilize an expression vector encoding TF antisense cDNA (Zhang et al., *J. Clin. Invest.* 97:2213, 1996; Bohrer et al., *J. Clin. Invest.* 100:972, 1997) or the antisense cDNA which encodes the rare tripeptide motif of Trp-Lys-Ser (WKS) (Stephens and Rivers, *Thromb. Res.* 85:387, 1997). Alternatively, one can utilize an expression vector or an oligonucleotide encoding a ribozyme targeting TF RNA.

Antisense Nucleic Acid Molecules

Treatment regimes based on an "antisense" approach involve the design of oligonucleotides (either DNA or RNA) that are complementary to a portion of a selected mRNA. These oligonucleotides bind to complementary mRNA transcripts and prevent their translation. Absolute complementarity, although preferred, is not required. A sequence "complementary" to a portion of an RNA molecule, as referred to herein, is a sequence having sufficient complementarity to hybridize with the RNA, forming a stable duplex; in the case of double-stranded antisense nucleic acids, a single strand of the duplex DNA can be tested, or triplex formation can be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One of ordinary skill in the art can ascertain a tolerable degree of mismatch by use of standard procedures to determine the melting point of the hybridized complex.

Oligonucleotides that are complementary to the 5' end of the message, for example, the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5' or 3' non-translated, non-coding regions of a TF gene, for example, a human gene as shown in FIG. 5, could be used in an antisense approach to inhibit translation of endogenous TF mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of TF mRNA, antisense nucleic acids should be at least six nucleotides in length, and are preferably oligonucleotides ranging from 6 to about 50 nucleotides in length (e.g., 8, 20, 30, or 40 nucleotides in length). In specific aspects, the oligonucleotide contains at least 10 nucleotides, at least 17 nucleotides, at least 25 nucleotides, or at least 50 nucleotides.

For example, the following antisense oligonucleotides can be used when treating dogs. 5'-GGGTCTTCATGGCCC-3' (SEQ ID NO:5), 5'-TACGACTACATCTG-3' (SEQ ID NO:6). The following antisense oligonucleotides can be used when treating humans. 5'-GGTCTCCATGTCTA-3' (SEQ ID NO:7), 5'-AAGACCCAGCCGAGCAGGA-3' (SEQ ID NO:8), and 5'-ACAGTATTTGTAGT-3' (SEQ ID NO:9).

Regardless of the choice of mRNA target sequence, as with other therapeutic strategies directed to TF, it is preferred that in vitro studies are first performed to assess the ability of an antisense oligonucleotide to inhibit gene expression. If desired, the assessment can be quantitative. It is preferred that these studies utilize controls that distinguish between antisense gene inhibition and any nonspecific biological effect that an oligonucleotide may incur. Preferably, the control oligonucleotide will be approximately the same length as the test oligonucleotide, and the nucleotide sequence of the control oligonucleotide will differ from that of the test antisense sequence no more than is necessary to prevent specific hybridization between the control oligonucleotide and the targeted RNA sequence. Preferably, these studies will also compare levels of the target RNA or protein with that of an internal control RNA or protein.

The oligonucleotides can contain DNA or RNA, or they can contain chimeric mixtures, derivatives, or modified versions thereof that are either single-stranded or double-stranded. The oligonucleotide can be modified at the base moiety, sugar moiety, or phosphate backbone, for example, to improve stability of the molecule, hybridization, etc. Modified sugar moieties can be selected from the group including, but not limited to, arabinose, 2-fluoroarabinose, xylulose, and hexose. A modified phosphate backbone can be selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The oligonucleotide can include other appended groups such as peptides (e.g., for disrupting the transport properties of the molecule in cells), or agents that facilitate transport across the cell membrane (as described, for example, in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, for example, a peptide, a hybridization triggered cross-linking agent, a transport agent, or a hybridization-triggered cleavage agent.

Antisense oligonucleotides of the invention can be synthesized by standard methods known in the art, for example, by use of an automated DNA synthesizer (such as are commercially available from Biosearch, Applied Biosystems, etc.).

In one application, antisense molecules can be delivered in vivo to the transplanted TF-expressing cells after they have been infused into a patient. A number of methods have been developed for delivering antisense DNA or RNA to cells; for example, antisense molecules can be injected directly into the tissue site. Accordingly, in the present case, if bone marrow cells are transplanted into a bone marrow cavity, the antisense molecules would be injected into that site as well. If bone marrow cells are transplanted into an intraarticular space, the antisense molecules would be applied to that space, and so forth. Alternatively, modified antisense molecules, which are designed to target cells that express TF (e.g., antisense molecules linked to peptides or antibodies that specifically bind to receptors or antigens expressed on the target cell surface) can be administered systemically.

Alternatively, or in addition to treating transplanted TF-expressing cells after they have been infused into a patient, the TF-expressing cells can be treated in vitro prior to transplantation. Thus, the patient initially receives cells that no longer express TF. This method is effective and simpler than administering the oligonucleotides to the patient.

Because it is often difficult to achieve intracellular concentrations of antisense molecules that are sufficient to suppress translation of endogenous mRNAs, a useful approach is to use a recombinant DNA construct in which the antisense oligonucleotide is placed under the control of a strong pol III or pol II promoter. The use of such a construct to transfect target cells (i.e., TF-expressing cells, whether before or after transplantation) will result in transcription of sufficient amounts of single stranded RNAs to form complementary base pairs with endogenous TF transcripts and thereby prevent translation of TF mRNA. For example, a vector can be introduced in such a way that it is taken up by a cell and thereafter directs the transcription of an antisense RNA. Such a vector can remain episomal or become chromosomally integrated, as long as it can be transcribed to produce the desired antisense RNA.

Vectors encoding a TF antisense sequence can be constructed by recombinant DNA technology methods that are standard practice in the art. Suitable vectors include plasmid vectors, viral vectors, or other types of vectors known or newly discovered in the art. The criterion for use is only that the vector be capable of replicating and expressing the TF antisense molecule in mammalian cells. Expression of the sequence encoding the antisense RNA can be directed by any promoter known in the art to act in mammalian, and preferably in human, cells. Such promoters can be inducible or constitutively active and include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

Ribozymes

Ribozyme molecules designed to catalytically cleave TF mRNA transcripts also can be used to prevent translation of TF mRNA and expression of TF polypeptides (see, for example, PCT Publication WO 90/11364; Sarver et al., *Science* 247:1222, 1990). While various ribozymes that cleave mRNA at site-specific recognition sequences can be used to destroy TF mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human TF cDNA (see FIG. 5A, for example at 181–182, 376–377, and 836–837). Preferably, the ribozyme is engineered so that the cleavage recognition site is located near the 5' end of the TF mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., *Science* 224:574, 1984; Zaug et al., *Science* 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in TF.

As in the antisense approach, the ribozymes can be composed of modified oligonucleotides (e.g., for improved stability, targeting, etc.), and can be delivered to TF-expressing cells either before or after they are transplanted into a patient. A preferred method of delivery involves using a DNA construct "encoding" the ribozyme under the control of a strong constitutive pol III or pol II promoter, so that transfected cells will produce sufficient quantities of the ribozyme to destroy endogenous TF messages and inhibit translation. Because ribozymes, unlike antisense molecules, are catalytic, a lower intracellular concentration is required for efficiency.

C. Reducing the Biological Activity of Tissue Factor by Administering Anti-Tissue Factor Antibodies The new methods can be carried out by administering antibodies that inhibit the biological activity of TF directly (i.e., by specifically binding TF) or indirectly (e.g., by blocking (in whole or in part) the association between TF and factor VII(a), or by reducing the activity of the TF-factor VIIa complex). These antibodies are referred to herein as "neutralizing" antibodies.

The cells expressing TF can be contacted with a neutralizing antibody in vitro or ex vivo, before they are transplanted into a patient to neutralize any TF on the surface of the cells. Thereafter, the antibody can be administered to the patient, e.g., by long-term infusion or repeat bolus injections, so that TF activity is reduced within the patient's bloodstream.

Neutralizing antibodies include anti-TF antibodies, anti-factor VII antibodies, or Fab fragments of such antibodies. Those of ordinary skill in the art will recognize the advantages of administering humanized forms of these antibodies.

Antibodies useful in this embodiment of the invention include, but are not limited to: (1) the polyclonal anti-TF antibodies described below in Example 2; (2) the polyclonal anti-TF antibodies described by Warr et al. (*Blood* 75:1481, 1990); (3) the polyclonal anti-TF antibodies described by Dackiw et al. (*Arch. Surg.* 131:1273, 1996); (4) the monoclonal anti-TF antibodies, TF1-E2 and TF1-F7, (Carson et al, *Blood* 66:152, 1985); (5) the monoclonal anti-TF antibody, HTF1-7B8 (Carson et al., *Blood* 70:490, 1987); (6) the monoclonal anti-TF antibody described by Taylor et al.(*Circ. Shock* 33:127, 1991); (7) the monoclonal anti-TF antibody, TF8-5G9 (Ruf and Edgington, *Thromb. Haemost.* 66:529, 1991); (8) the monoclonal anti-TF antibodies, TF8-11D12 and TF9-9C3 (Fiore et al., *Blood* 80:3127, 1992); (9) the monoclonal anti-TF antibody, TF8-5G9 (Levi et al., *J. Clin. Invest.* 93: 114, 1994); (10) the monoclonal anti-TF antibody, AP-1 (Himber et al., *Thromb. Haemost.* 78:1142, 1997); (11) the monoclonal anti-TF antibody, 5G9 (Huang et al., *J. Mol. Biol.* 275:873, 1998); (12) the monoclonal anti-Factor VII antibody, PW-4 (Wildgoose et. al., *Thromb. Haemost.* 67:679, 1992); (13) the monoclonal anti-factor VII antibody, 231–7 (Clarke et al., *FEBS Lett.* 298:206, 1992); (14) the monoclonal anti-factor VII antibody, 12D10 (Biemond et al., *Thromb. Haemost.* 73:223, 1995) and; (15) the monoclonal anti-factor VII antibodies, hVII-B101/B1, hVII-DC2/D4 and hVII-DC6/3D8 (Takamiya, *Thromb. Haemost.* 79:104, 1998).

Alternatively, antibodies can be raised against TF or factor VII (or immunogenic fragments or analogs thereof) by techniques well known in the art. Antigenic polypeptides can be produced by recombinant techniques or synthesized and, once obtained in substantially pure form, mixed with an adjuvant and injected into a host mammal (such as a rabbit, mouse, guinea pig, or rat). The adjuvant used to increase the immunological response will depend on the host mammal. Adjuvants can be selected from Freund's adjuvant (complete or incomplete), mineral gels (e.g., aluminum hydroxide), surface active substances (e.g., lysolecithin), pluronic polyols, polyanions, peptides, oil emulsions, keyhole limpet hemocyanin, and dinitrophenol. Potentially useful human adjuvants include BCG (bacille Calmette-Guerin) and *Corynebacterium parvum.* The heterogeneous antibody molecules contained in the sera of the immunized animals (i.e., polyclonal antibodies) can then be purified by peptide antigen affinity chromatography.

In addition to the polyclonal antibodies described above, monoclonal antibodies, humanized or chimeric antibodies, single chain antibodies, Fab fragments, F(ab')$_2$ fragments, and molecules produced using a Fab expression library can be used in the new methods described herein.

Monoclonal antibodies, which are homogeneous populations of antibodies to a particular antigen, can be prepared using TF or factor VII polypeptides and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific TF or factor VII recognition by Western blot or immunoprecipitation analysis by standard methods, for example, as described in Ausubel et al., eds. *Current Protocols in Molecular Biology,* John Wiley & Sons, N.Y., 1987, 1989.

In addition, one can use techniques developed for the production of "chimeric antibodies" by splicing a gene encoding an antibody molecule of appropriate antigen specificity from one animal species (e.g., a mouse) together with genes from a human antibody molecule of appropriate biological activity (Morrison et al., *Proc. Natl. Acad. Sci. USA* 81:6851, 1984; Neuberger et al., *Nature* 312:604, 1984; Takeda et al., *Nature* 314:452, 1984). Thus, a chimeric antibody could have a variable region derived from a murine mAb and a human immunoglobulin constant region.

Alternatively, one could use techniques for producing single chain antibodies (e.g., as described in U.S. Pat. Nos. 4,946,778, 4,946,778, and 4,704,692) to produce single chain antibodies against a TF polypeptide, a factor VII polypeptide, or fragments thereof. Single chain antibodies are formed by linking the heavy and light chain fragments of the Fv region via an amino acid bridge, resulting in a single chain polypeptide.

Moreover, antibodies can be humanized by methods known in the art. For example, monoclonal antibodies with a desired binding specificity can be humanized by commercial service providers such as Scotgene (Scotland) and Oxford Molecular (Palo Alto, Calif.). Fully human antibodies can also be expressed in transgenic animals according to the methods described by Green et al. (*Nature Genetics* 7:13–21, 1994; see also U.S. Pat. Nos. 5,545,806 and 5,569,825).

D. Reducing the Biological Activity of Tissue Factor by Administering Peptides The new methods can also be carried out by administering to the patient peptides (naturally-occurring or synthetic) that inhibit TF activity, its association with factor VII(a) or the activity of the TF-factor VIIa complex. As described above in relation to the use of antisense oligonucleotides, ribozymes, and neutralizing antibodies, the cells expressing TF can be contacted with a peptide antagonist in vitro or ex vivo, before they are transplanted into a patient. However, peptide antagonists can also be administered to the patient so that TF activity is reduced in the bloodstream. More generally, any molecule that directly or indirectly antagonizes TF (i.e., any molecule that antagonizes the expression or activity of TF or that antagonizes the expression or activity of any factor, such as factor VII, that interacts with TF) can either be applied to the cells used in the present methods (e.g., BMSCs) ex vivo, prior to transplantation, or administered to the patient.

Peptides useful in this embodiment of the invention include, but are not limited to: (1) the factor VII Gla-peptide, FVII-GP (Wildgoose et. al., *Thromb. Haemost.* 67:679, 1992); (2) the peptide analog of TF, TF154–167 (Ronning et. al., *Thromb. Res.* 84:73, 1996); (3) the peptide analog of factor VII, FVII300–305 167 (Ronning et. al., *Thromb. Res.* 84:73, 1996); (4) peptides possessing the tripeptide motif Trp-Lys-Ser (Ronning et. al., *Thromb. Res.* 84:73, 1996); (5) peptide analogs of epidermal growth factor-like domains of factor VII, including the sequence Cys-Val-Asn-Glu-Asn-Gly-Gly-Cys-Glu-Gln-Tyr-Cys (SEQ ID NO:10) and; (6) peptides bearing the tripeptide motif Glu-Gln-Tyr (Orning et al., *Thromb. Res.* 86:57, 1997).

E. Reducing the Biological Activity of Tissue Factor by Administering Modified Coagulation Factors In another embodiment, the new methods can be carried out by administering to the patient modified or abnormal coagulation factors (naturally-occurring or recombinant) that inhibit TF activity, its association with factor VII(a) or the activity of the TF-factor VIIa complex. These factors include, but are not restricted to: active-site inactivated recombinant factor VIIa, FVIIai (Harker et al., *Haemostasis* 26 Suppl. 1:76, 1996); modified recombinant factor VIIa; dansyl-glutamyl-glycyl-arginyl-recombinant FVIIa (DEGR-rFVIIa) (Orvim et al., *Arterioscler. Thromb. Vasc. Biol.* 17:3049, 1997); active-site inactivated modified factor VIIa; D-Phe-L-Phe-L-Arg-chloromethyl ketone treated Factor VIIa (FFR-FVIIa) (Kjalke et al., *Thromb. Haemost.* 78:1202, 1997); purified abnormal factor IX, factor IXBm (Osterud et al., *Thromb. Haemost.* 45:55, 1981) and; native or modified TF pathway inhibitor (TFPI).

TFPI appears to be the major physiologic inhibitor of TF-induced coagulation (Bajaj and Bajaj, *Thromb. Haemost.* 78:471, 1997). TFPI has been referred to as anti-convertin, external pathway inhibitor (EPI), and lipoprotein-associated coagulation inhibitor (LACI) (Merstraete and Zoldhelyi, *Drugs* 49:856, 1995). Recombinant forms of truncated TFPI, such as the TFPI$_{1-161}$ have been disclosed (Petersen et al., *J. Biol. Chem.* 268:13344, 1993).

A second TF pathway inhibitor (TFPI-2), which has considerable amino acid sequence homology to TFPI, and which is identical to placental protein 5 (PP5) (Petersen et al., *Biochemistry* 35:266, 1996), is also useful in the new methods described herein.

F. Reducing the Biological Activity of Tissue Factor by Administering Lipocortins The new methods can be carried out by administering native or modified members of the lipocortin family to the patient before, during, or after the TF-expressing cells are implanted. For example, one can administer: Annexin V (which was previously isolated and identified as placental anticoagulant protein (PAP)); vascular anticoagulant-alpha (VAC); endonexin II; lipocortin V; placental protein 4; and anchorin CII (Tait et al., *Cytogenet. Cell Genet.* 57:187, 1991). PAP has been shown to inhibit factor VIIa-TF activity, most likely by binding to the phospholipid portion of the TF lipoprotein (Kondo et al., *Thromb. Res.* 48:449, 1987). Annexin V is also referred to as calcium dependent phospholipid binding protein-1 (CPB I).

Peptides corresponding to PAP residues 204–209 (SHLRKV; SEQ ID NO:11) and 266–271 (DHTLIR; SEQ ID NO:12), which are included in the PAP functional site, exhibit anticoagulant activity (Funakoshi et al., *Biochem. Int.* 24:173, 1991).

Calphobindin II (CPB-II) and Calphobindin III (CPB-III) also exhibit anticoagulant activity (Yoshizaki et al., *Chem. Pharm. Bull* (Tokyo) 40:1860, 1992; Sato, *J. Exp. Med.* 168:561, 1992).

G. Reducing the Biological Activity of Tissue Factor by Administering Modified Lipids, Apolipoproteins or Phospholipase The new methods can be carried out by administering native or modified lipids, apolipoproteins, or phospholipase (natural or recombinant). For example, sphingosine inhibits TF initiated coagulation by modulating factor VII binding to TF (Conkling et al., *J. Biol. Chem.* 264:18440, 1989). Apolipoprotein A-II inhibits TF participation in the activation of coagulation factor X by factor VIIa by preventing the appropriate association of TF with factor VIIa (Carson, *J. Bio. Chem.* 262:718, 1987). Apolipoprotein B-100 inhibits TF activity (Ettelaie et al., *Arterioscler. Thromb. Vasc. Biol.* 16:639, 1996). Recombinant peptides representing lysine-rich regions of apolipoprotein B-100 (KRAD-98 and KRAD-14) inhibit procoagulant activity of TF by preventing the activation of factor VII (Ettelaie et al., *Biochem. J.* 333 (Pt 2):433, 1998). Phospholipase C inhibits TF induced coagulation (Jansson et al., *J. Trauma* 28 (1 Suppl):S222, 1988).

H. Reducing the Biological Activity of Tissue Factor by Administering Modified Polysaccharides The methods of the invention can be carried out by administering native or modified polysaccharides that act as inhibitors of binding of TF to other coagulation factors. For example, the synthetic pentasaccharide is homologous to heparin sequences that bind to antithrombin. The pentasaccharide binds to antithrombin, thereby stimulating the antithrombin inhibition of TF-factor VIIa complex. Thus, a synthetic pentasaccharide representing the minimal binding site of heparin to antithrombin is an efficient antithrombin-dependent inhibitor of the coagulant activity of TF-factor VIIa complex (Lormeau et al., *Thromb. Haemost.* 76:5, 1996).

I. Reducing the Biological Activity of Tissue Factor by Administering Agents that Act Downstream from the Tissue Factor-Factor VII Complex In another embodiment, the methods can be carried out by administering to the patient antithrombotic, anticoagulant agents, which act upon coagulation factors downstream of the activity of TF-factor VII complex prior to, during, or following the infusion (or other administration) of TF-expressing cells. These agents act by inhibiting coagulation factors or by inhibiting platelet activation. The following agents are discussed in the reviews by Verstraete and Zoldhelyi (*Drugs* 49:856, 1995) and Carey and Rodgers (*Am. J. Hematol.* 59:65, 1998) unless otherwise referenced:

Native or modified polypeptides that are involved in anticoagulation regulation: antithrombin III (wild type antithrombin III, antithrombin III containing mutated residues in the reactive center loop, antithrombin III containing mutations in the heparin binding site); thrombomodulin; activated Protein C (with or without protein S); recombinant $\alpha_1$-antitrypsin-Pittsburgh, a mutant protease inhibitor of thrombin; phospholipase A2, or synthetic peptides comprising residues 51–74 and 51–62 of phospholipase S2 (Mounier et al., *J. Biol. Chem.* 273:23764, 1998); snake venom disintegrin polypeptides (e.g., kristin, bitistasin, applaggin, echistatin, trigamin, barbourin); polypeptides of antithrombin produced by the salivary glands of the leech (e.g., hirudin, desulphatohirudin, hirulog, hirugen, hirudisins, rHV2, rHV2-Lys47, rHV2-Arg47, antistasin); tick anticoagulant peptide (TAP); hookworm anticoagulant peptides (forms of AcAP); Arg-Gly-Asp (RGD) or Arg-Gly-Asp-Ser (RGDS; SEQ ID NO:13) peptides, or polypeptides that bearing these peptide sequences and prevent platelet activation; the boroarginine tripeptide DUP714, or a bi-O-Tyr-sulfated decapeptide (NF-6505) (Sasaki et al., *Thromb. Res.* 86:453, 1997), which bind to thrombin; antibodies (or Fab fragments, or humanized antibodies) to platelet GPIIb/IIIa (e.g., c7E3 Fab, abciximab), platelet GPIb, multimeric von Willebrand factor, or factor X (alpha BFX-2b) (Church et al., *Blood* 72:1911, 1988).

Nonpeptide agents that have anticoagulation, antithrombotic, or antiplatelet-activation activities:

Thienopyridine derivatives (e.g., ticlopidine, clopidogrel) that inhibit platelet aggregation; antiplatelet agent triflusal and its active 3-hydroxy-4-trifluoro-methylbenzoic acid metabolite (McNeely and Goa, *Drugs* 55:823, 1998); platelet activating factor antagonists (e.g., SM-12502 (Murakami et al., *Thromb. Haemost.* 75:965, 1996); nonpeptide inhibitors of GPIIb/IIIa (e.g., tirofiban (MK-383), SC-5468A); fibrinogen receptor antagonists (e.g., fradafibran (BIBU 104XX), BIBI 52ZW); thromboxane synthase inhibitors, thromboxane receptor antagonists (e.g., daltroban, ifetroban) and compounds with dual activity (e.g., ridogrel, picotamide) prostacyclin analogues (e.g., iloprost, epoprostenol); antithrombotic sulodexide; antithrombins argatroban; RWJ-27755; efegatran; or BCH-2763 (Finkle et al., *Thromb. Haemost.* 79:431, 1998); or inogatran (Gustafsson et al., *Blood Coagul. Fibrinolysis* 7:69, 1996); inhibitors of factor Xa such as the pentasaccharides Org 31540/SR 90107A and SANORG 32701, and a bis-amidinoderivative DX-9065a (Yamazaki et al., *Semin. Thromb. Hemost.* 22:255, 1996), or APAP (Yokoyama et al., *Circulation* 92:485, 1995); heparin, low molecular weight heparins, heparinoids or low molecular weight heparinoids (Gibaldi and Wittkowsky, *J. Clin. Pharmacol.* 35:1031, 1995); aspirin (Schror, *Semin. Thromb. Hemost.* 23:349, 1997) gabexate mesilate (Umeki et al., *Arch. Intern. Med.* 148:1409, 1988); the protease inhibitor aprotinin (Svartholm et al., *Acta. Chir. Scand.* 155:7, 1989), and derivatives 4C2, 7L22, 5L15, 5L15-PEG, 6L15 and 5L84 (Stassen et al., *Thromb. Haemost.* 74:655, 1995).

The expression of TF in cells such as BMSCs can also be reduced by culturing, or incubating, the cells in specific agents such as transmethylation inhibitors (e.g., DZA, DZAri, EHNA; Dalaker and Prydz, *Biochem. Pharmacol.* 35:3433, 1986); calcium antagonists (e.g., TMB-8, verapamil, nifedipine, felodipine; Dalaker and Prydz, supra); prostaglandin E2 (PGE2; Dalaker and Prydz, supra); phosphodiesterase inhibitor (e.g., MIX (Dalaker and Prydz, supra), pentoxifylline and trequinsin (Leclerc et al., *J. Cardiovasc. Pharmacol.* 25 Suppl 2:S88, 1995); monensin (Dalaker and Prydz, supra); prostacyclin and prostacyclin analogues (e.g., iloprost, ciprostene, carbacyclin; Crutchley et al., *Arterioscler. Thromb.* 12:664, 1992); NF kappa B pathway inhibitors (e.g., dithiocarbamates; Orthner et al., *Blood* 86:436, 1995); curcumin (Bierhaus et al., *Thromb. Haemost.* 77:772, 1997); and interleukins (e.g., IL-4, IL-10, IL-13, TGF-β; Ernofsson et al., *Br. J. Haematol.* 95:249, 1996).

J. Effective Dose

As described above, antagonists of TF can be administered to a patient to reduce or inhibit the expression or activity of TF. The standard dosages and known therapeutically effective amounts (e.g., an amount effective to reduce adverse vascular effects caused by TF) of the antagonists described herein can be used. Toxicity and therapeutic efficacy of these antagonists can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue (e.g., the bone marrow cavity into which cells have been infused) to minimize potential damage to uninfected cells and, thereby, reduce side effects.

The data obtained from the cell culture assays and animal studies can be used in formulating a range of dosages for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

K. Formulations and Use

The TF antagonists described above can be formulated for administration to a patient in a conventional manner using one or more physiologically acceptable carriers or excipients. Thus, the antagonists (i.e., the nucleic acids, polypeptides, antibodies, or other TF modulatory compounds of the invention) or their physiologically acceptable salts and solvates may be formulated for administration by any standard route of administration. For example, administration can be parenteral, intravenous, subcutaneous, intramuscular, intracranial, intraorbital, ophthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

EXAMPLES

Example 1

Infusion of Autologous Canine Bone Marrow Stromal Cells is Associated with Intravascular Thrombosis Canine bone marrow stromal cells (BMSCs) were cultured as described by Emami et al. (*In Vitro Cellular & Developmental Biology-Animal* 33:503, 1997) and Hurwitz et al. (*Human Gene Therapy* 8:137, 1997). These cultures were devoid of hematopoietic progenitor cells (Hurwitz et al., supra).

Cultured BMSCs can be genetically modified and infused into animals. For example, BMSCs can be genetically modified to express human growth hormone, human factor IX, canine factor IX, or human factor VIII (See U.S. Pat. No. 5,849,287). When BMSCs are harvested from an animal, cultured, and infused into the same animal, the procedure is referred to as autologous re-infusion. Successful re-infusion with $1.9 \times 10^7 - 5.6 \times 10^8$ BMSCs has been performed on dogs (weighing 20–27.4 kg) on at least 17 separate occasions, including those described by Hurwitz et al. (supra) and Cherington et al. (*Human Gene Therapy* 9:1397, 1998). However, on one occasion, when a dog (designated #2) weighing 26.3 kg received $2.6 \times 10^9$ BMSCs, adverse side effects were observed (Hurwitz et al., supra). The dog had difficulty breathing and some blood appeared in its stool. On a second occasion, using the methods described by Cherington et al. (supra), a dog (designated #20A) weighing 23.6 kg received $8.8 \times 10^8$ BMSCs by autologous re-infusion (the cells were modified to express human factor IX) and experienced severe side effects. Consequently, the dog was euthanized. An autopsy revealed extensive interstitial capillary thrombosis and resultant hemorrhage due to an intravascular coagulation.

The adverse reactions described above were unexpected because bone marrow preparations that are commonly used in bone marrow transplantation procedures contain bone marrow stromal cells, and there was no reason to suspect that infusing pure populations of stromal cells would cause adverse reactions.

Figure 2:
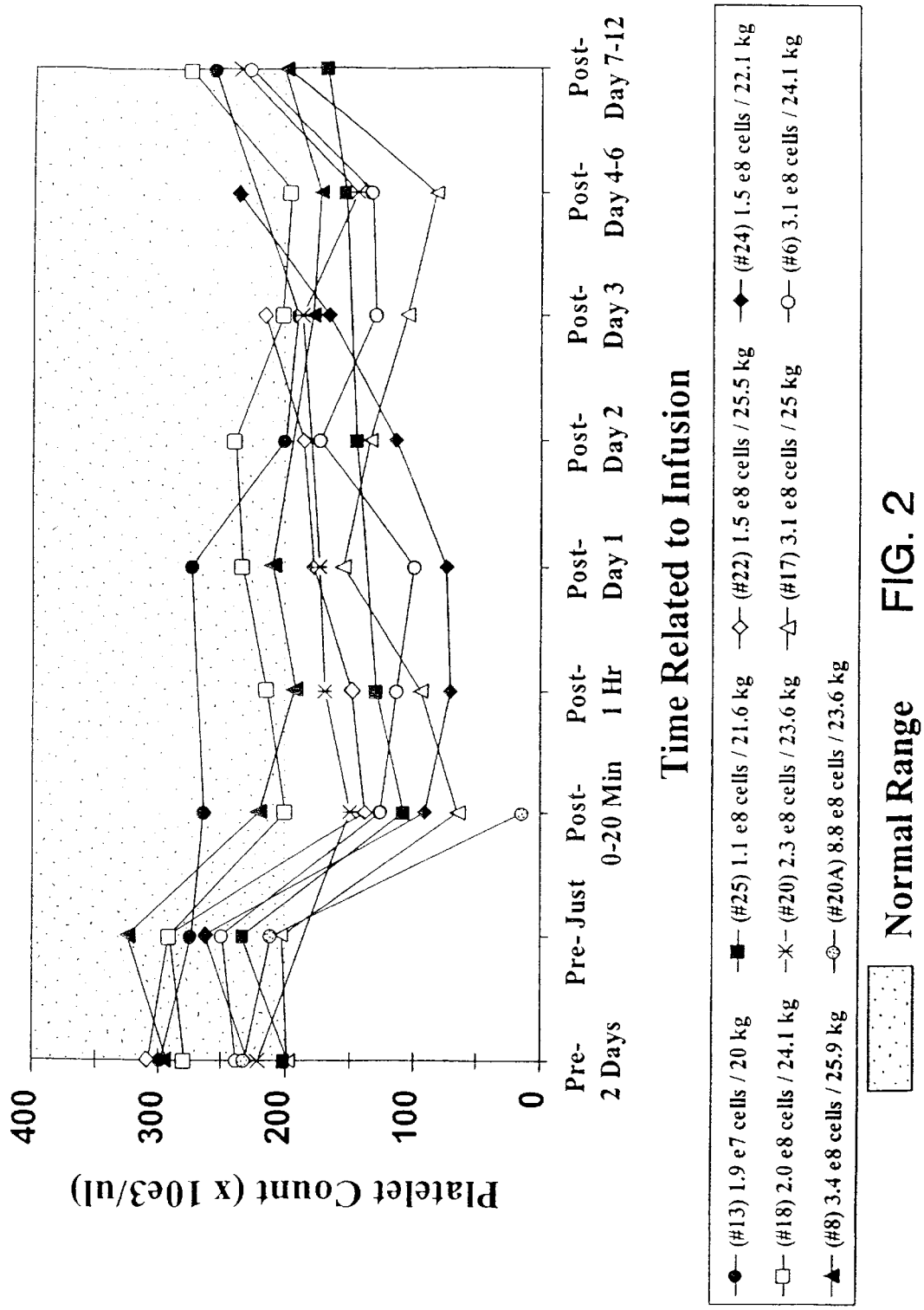
FIG. 2 is a line graph depicting platelet counts ($\times 10^3/\mu l$) in ten dogs (each represented by a distinct symbol) before and at various times after infusion of autologous BMSCS. The number of cells infused into each animal is shown in the box beneath the graph.

To evaluate the adverse effects, blood platelet counts were obtained before and at various times after dogs (n=10) received autologous BMSC infusions (FIG. 2). Within 20 minutes following the infusion of cells, the majority of the dogs experienced a drop in platelet count. Moreover, there was an evident correlation between the number of cells infused and the drop in platelet count; the greater the number of cells, the greater the drop in platelets. The level of blood platelets was restored to normal or near normal levels within 7–12 days following infusion of BMSCs (with the exception of dog #20A, which was euthanized).

Figure 3:
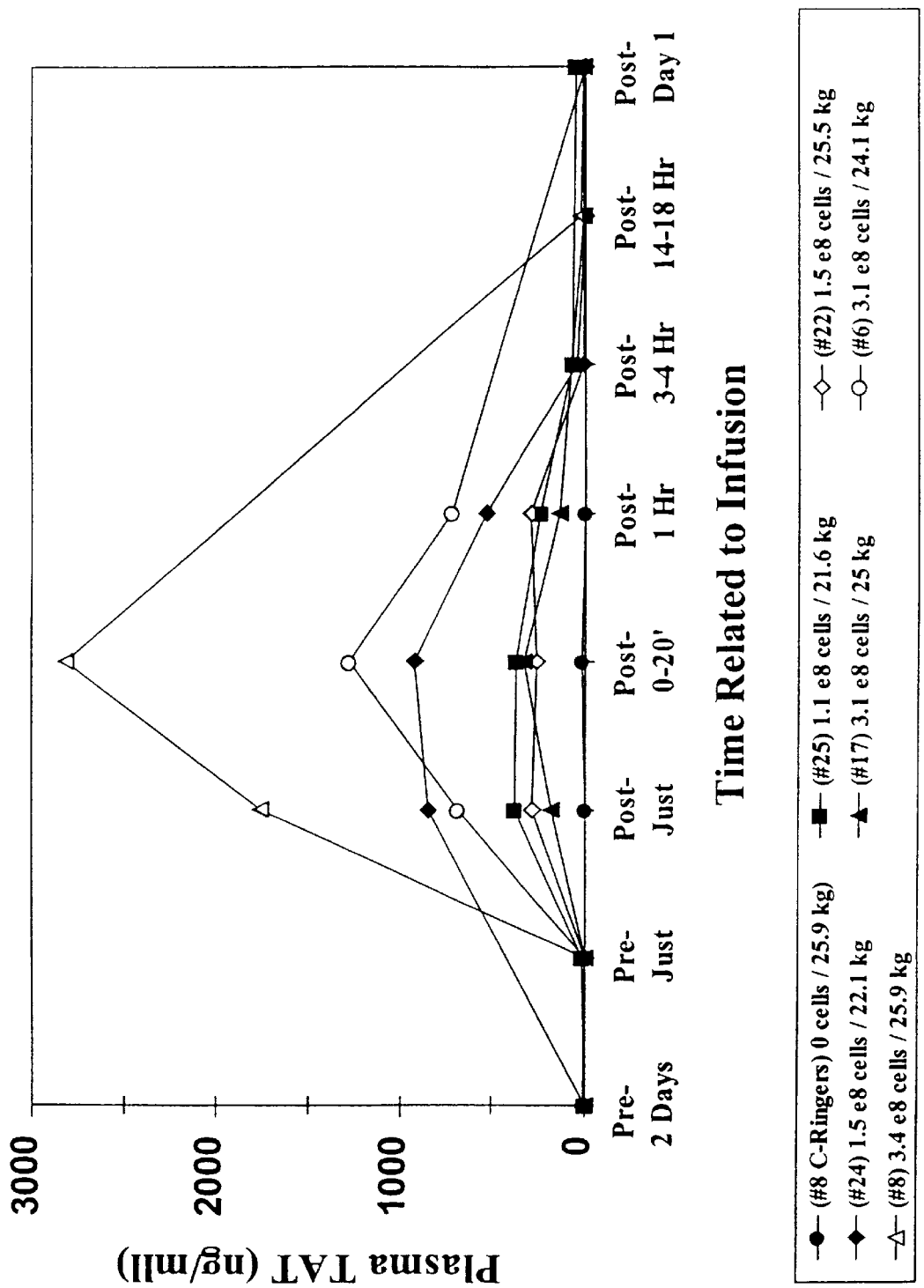
FIG. 3 is a line graph depicting the concentration of thrombin-antithrombin (TAT; ng/ml) in the plasma of seven dogs (6 experimental animals and one control (•=#8)) following infusion of autologous BMSCs. Each of the seven symbols represents data obtained from one animal, and the number of cells infused into each animal is shown in the box beneath the graph.

In addition, plasma levels of thrombin-antithrombin (TAT) were determined by Colorado Coagulation Consultants (Aurora, Colo.) following the infusion of BMSCs into six animals (see FIG. 3). TAT levels began to rise at the time of infusion, peaked at approximately 20 minutes post-infusion, and then declined. TAT levels returned to normal within one day of infusion of BMSCs. These data reveal an evident correlation between the number of cells infused and TAT levels; the greater the number of cells, the greater the level of TAT.

These studies (analyzing platelet and TAT levels) indicated that the adverse side effects seen following BMSC infusion may have been due to infusion of high numbers of BMSCs.

To determine the cause of the adverse reactions, BMSCs were analyzed in a number of ways. Following is a description of studies that demonstrated expression of TF in BMSCs. While not wishing to be bound by any one underlying mechanism, this expression could account for the adverse reactions that occurred when large numbers of BMSCs were re-infused on the two occasions described above.

Example 2

Canine Bone Marrow Stromal Cells Express Tissue Factor RNA

RNA was isolated from canine BMSCs, which were established in tissue culture, by the Tri Reagent™ system (Sigma Chemical Company, St. Louis, Mo.). To remove any trace of contaminating DNA, the isolated RNA was digested for 3 hours with RNAse-free DNAse (Promega Corporation, Madison, Wis.) as follows: 10 $\mu$l of 100 mM $MgCl_2$, 10 mM DTT, 0.2 $\mu$l of 2.5 mg/ml RNAse-free DNAse, 0.1 $\mu$l RNAsin (50 U/$\mu$l) and 39.7 $\mu$l of TE (pH 7.2) were added to 50 $\mu$l of RNA. The sample was then extracted with phenol/chloroform and the RNA was precipitated with ethanol and resuspended in TE (pH 7.2). The concentration of RNA recovered was then determined by measuring the OD at 260 nm.

To generate cDNA, RT-PCR was carried out using 1 $\mu$g of RNA and the Promega Reverse Transcriptase System (Promega Corporation) according to the manufacturer's protocol. TF cDNA was then amplified by the PCR. The cDNA was initially denatured at 94° C. (for 5 minutes) and amplified by 35 cycles of denaturation (940° C. for 30 seconds), annealing (58° C. for 50 seconds) and elongation (72° C. for 90 seconds), followed by a final elongation step (72° C. for 5 minutes). The PCR primers were human TF sequence primers in TF cDNA protein coding regions that are homologous between human (Spicer et al., *Proc. Natl. Acad. Sci. USA* 84:5148, 1987) and mouse (Ranganathan et al., *J. Biol. Chem.* 266:496, 1991) TF cDNA sequences. The sequences of the 5' and 3' primers were 5'-ATTTCAAGACAATTTTGGAGTGG-3' (SEQ ID NO:14, and 5'-AGTTTTCTCCTTTATCCACATC-3' (SEQ ID NO:15), respectively. The 5' primer is homologous to the 260–282 base pair (bp) and 165–187 bp positions of the human and mouse TF cDNA sequences, respectively. The 3' primer is homologous to the 683–662 bp and 760–739 bp positions of the human and mouse TF cDNA sequences, respectively. The size of the TF-specific RT-PCR band generated using human or mouse RNA as templates would be 424 bp or 596 bp, respectively. PCR products were resolved on 1% agarose gels and visualized by ethidium bromide staining.

The RT-PCR performed on RNA isolated from canine BMSCs produced a band of the expected size of ~424–596 bp. It was slightly smaller than a 603 bp marker band (Hind III-digested $\lambda$ and Hae III-digested $\phi$X174 DNA markers) and the same size as bands generated using RNA isolated from canine brain or canine MDCK cells, both of which are known to express TF). A band generated using a human TF cDNA plasmid as template was somewhat smaller, as expected. A negative control sample, which was generated by performing a reaction without template DNA, did not produce an appropriately sized band.

This study demonstrated that canine BMSCs express TF RNA.

Example 3

Cloning and Sequencing Experiments Confirm Expression of Tissue Factor RNA in Canine BMSCs The RT-PCR product generated as described above (from RNA isolated from canine BMSCs), was cloned into the TA vector (InVitrogen Corporation, San Diego, Calif.) according to manufacturer's instructions, and sequenced. The sequence was homologous to regions of the human and mouse TF sequences that are homologous to one another (moreover, in regions where the human and mouse sequences were not homologous, the homology of the canine sequence diverged as well).

The full-length sequence of canine TF RNA was obtained by using the Marathon™ cDNA Amplification Kit (Clonetech Laboratories, Inc., Palo Alto, Calif.). First strand cDNA synthesis was carried out using a lock-docking oligo (dT) primer, and second strand cDNA synthesis was carried out using E. coli DNA polymerase I and ligation with a 5' extended double stranded adaptor, according to manufacturer's instructions. The 5' end of the TF cDNA (about ⅓ of the complete cDNA) was amplified by 5'-RACE PCR using the Marathon™ cDNA Amplification Kit in combination with the Advantage-GC™ cDNA PCR Kit (Clonetech). The reaction included an AP1 5'-primer and a canine TF-specific 3'-primer (5'-ATCTTGTACGATCACATTC-3' SEQ ID NO:16) in 1×GC melt and 1×Advantage PCR buffer. Following denaturation (940° C. for 5 minutes), amplification was achieved by 35 cycles of denaturation (94° C. for 30 seconds), annealing (58° C. for 50 seconds) and elongation (72° C. for 90 seconds) followed by a final elongation step (72° C. for 5 minutes). The 3' end of the TF cDNA (about ⅔ of the complete cDNA) was amplified by 3'-RACE PCR using the Marathon™ cDNA Amplification Kit in combination with the Advantage™ cDNA PCR Kit (Clonetech) using a TF specific 5'-primer (5'-ATTTCAAGACAATTTTGGAGTGG-3' SEQ ID NO:17) and an AP1 3' primer in 1×Advantage™ PCR buffer. The amplification conditions were the same as those described immediately above. Both of the amplified fragments were cloned to the TA™ vector (Invitrogen) according to manufacturer's instructions, and sequenced by standard procedures.

The cDNA and predicted amino acid sequences are shown in FIG. 4. The complete cDNA sequence consists of an open reading frame of 879 bp flanked by 110 bp of 5'-UTR and 850 bp of 3'-UTR. The open reading frame, which is clearly highly homologous to human TF, encodes canine TF.

These studies confirm that canine bone marrow stromal cells express TF RNA, and reveal the sequence of that factor.

Example 4

Canine BMSCs Possess Tissue Factor Activity

Canine BMSCs were grown in culture and tested for TF procoagulant activity. Cells that had been transduced to express transgene products as well as those in naive cultures were tested.

To assay for total TF activity in BMSC cultures, BMSCs were harvested by trypsinization, washed twice in phosphate-buffered saline (PBS), and pelleted by centrifugation. The cell pellet was resuspended in PBS to approximately 1×10⁶ cells/ml. Cell suspensions were quick frozen in liquid nitrogen (approximately 40 seconds) and either stored at −80° C. or tested immediately. In either event, the cells were lysed by three freeze-thaw cycles and TF activity was determined in the cell lysate by the clotting assay procedure of Camerer et al. (Blood 88:1339, 1996). Canine normal pooled plasma, the Automated Coagulation Laboratory (ACL)-3000 plus apparatus (Instrumentation Laboratories, Lexington, Mass.; the aPTT program) and lipidated recombinant human TF (American Diagnostica, Greenwich, Conn.) were used to generate a TF activity standard curve.

As shown in Table 1, BMSC cultures established from several dogs possess TF activity, regardless of whether they consist of cells that have been transduced to express transgene products (human factor IX or canine factor IX), or cells that are naive to genetic modification.

The BMSC cultures used to generate the data shown in Table 1 were established and grown in culture as described by Hurwitz et al. (Human Gene Therapy 8:137, 1997). The methods for BMSC transduction and the vectors used were those described in Cherington et al. (Human Gene Therapy 9:1397, 1998). Briefly, the MFG-hFIX vector encodes human factor IX and the MFG-cFIX vector encodes canine factor IX. And the TF activity was determined in the cell lysate by the clotting assay procedure of Camerer et al. (Blood 88:1339, 1996) using canine normal pooled plasma, the Automated Coagulation Laboratory (ACL)-3000 plus apparatus (Instrumentation Laboratories, Lexington, Mass.), using the aPTT program, and lipidated recombinant human TF (American Diagnostica Inc., Greenwich, Conn.) to generate a TF activity standard curve.

TABLE 1

Tissue Factor Activity Levels in Naïve and Vector Transduced Canine Bone Marrow Stromal Cells

| Dog # From Which Stromal Cells were Cultured | Vector Used to Transduce Cultured Stromal Cells | Tissue Factor Activity Levels (ng/10⁶ cells) |
| --- | --- | --- |
| #18 | Not Transduced | 209 |
| #21 | Not Transduced | 68.9 |
| #24 | Not Transduced | 1,307 |
| #6 | MFG-hFIX | 1,757 |
| #8 | MFG-hFIX | 655 |
| #17 | MFG-cFIX | 138 |
| #20 | MFG-cFIX | 332 |

The conclusion—that procoagulant activity found in canine BMSCs is due to expression of canine TF—is considerably strengthened by two findings: (1) antibodies that specifically inhibit human TF activity inhibit TF activity in canine BMSC lysates (see Table 2), and antibodies that specifically inhibit factor VII activity inhibit the BMSC lysate TF procoagulant activity (Table 3).

Reagents used to generate the data shown in Table 2 included human recombinant TF (American Diagnostica, Greenwich, Conn.); non-specific rabbit immunoglobulin (DAKO A/S, Glostrup, Denmark; used at a concentration of 125 µg/250 µl); and specific rabbit anti-human TF IgG (American Diagnostica, Greenwich, Conn; used at a concentration of 125 µg/250 µl). Human recombinant TF (250 µl) or canine stromal cell lysate (250 µl), each at a concentration of approximately 40 ng/ml of TF activity, were preincubated with 250 µl of the indicated reagent (see the left-hand column of Table 2) for 30 minutes at 37° C. prior to the TF activity assay. The expected final TF activity would be 20 ng/ml if it was not inhibited. The TF activity was determined as described above (Camerer et al.).

TABLE 2

Inhibition of Tissue Factor Procoagulant Activity In Canine Bone Marrow Stromal Cells by Anti-Tissue Factor Specific Antibodies

| | Human Recombinant TF | | Canine BMSC Lysate | |
| --- | --- | --- | --- | --- |
| Pre-Incubation Reagent | Tissue Factor Activity (ng/ml) | Percent Inhibition | Tissue Factor Activity (ng/ml) | Percent Inhibition |
| PBS Buffer | 22.9 | — | 18.7 | — |
| Non-Specific Rabbit Immunoglobulin | 22.6 | 1.3% | 20.3 | 0% |
| Specific Rabbit Anti-Human Tissue Factor IgG | 0.9 | 96.1% | 2.0 | 89.3% |

Reagents used to generate the data shown in Table 3 included human normal pool (HNP) and factor VII deficient plasma (George King Bio-Medical Inc., Overland Park, Kans.), $CaCl_2$ (Instrumentation Laboratories, Lexington, Mass.), mouse IgG1 kappa (PharMingen, San Diego, Calif., at 0.5 mg/ml in PBS), and mouse anti-human factor VII/VIIa, which is a mouse IgGI kappa isotype (American Diagnostica, Greenwich, Conn., at 0.5 mg/ml in PBS). The indicated concentrations of PBS, mouse IgG1, or mouse anti-human factor VII were pre-incubated with HNP for 30 minutes at room temperature with agitation. The range of PBS concentrations correspond to the range of mouse IgG or antibody preparations added to HNP. Assays for TF procoagulant activity were performed on an ACL-3000 plus coagulation analysis system using the APTT program (described above). Canine BMSC lysate replaced the Cephalin reagent in position #2.

TABLE 3

Inhibition of Canine bone Marrow Stromal Cell-Derived Tissue Factor Procoagulant Activity By Anti-Factor VII Antibodies

| Assay components | Human plasma pre-incubated with: | Concentration of Reagent pre-incubated with plasma (per 0.5 ml) | Plasma Clotting Time (seconds) Individual assays or average ± SD of (n) determinations |
| --- | --- | --- | --- |
| HNP, BMSC lysate, $CaCl_2$ | N.A. | N.A. | 39.0 ± 5.1 (6) |
| F7-deficient human plasma, BMSC lysate, $CaCl_2$ | N.A. | N.A. | 85.2, 100, >120, >120 |
| HNP, PBS, $CaCl_2$ | N.A. | N.A. | >120 |
| HNP, BMSC lysate, $CaCl_2$ | PBS | 10–50 µl | 45.8 ± 1.6 (6) |
| HNP, BMSC lysate, $CaCl_2$ | Mouse IgG1K | 25.9 µg | 39.9, 44.8 |
| | | 12.5 µg | 41.2, 44.5 |
| | | 7.5 µg | 45.8 |
| | | 5.0 µg | 40.4, 43.6 |
| HNP, BMSC lysate, $CaCl_2$ | Mouse anti-hFVII/FVIIa | 25.0 µg | >120, >120 |
| | | 12.5 µg | >120, >120 |
| | | 7.5 µg | 105 |
| | | 5.0 µg | 92.5, 97.8 |

Example 5

Tissue Factor Expression in Cultured Canine BMSCs is Evident Following Immunoassay

Homogenous populations of canine BMSCs were cultured as previously described (Emami et al., *In Vitro Cellular & Developmental Biology-Animal* 33:503, 1997 and Hurwitz et al., supra) and subjected to immunofluorescence analysis using antibodies specific to TF.

Tissue culture adherent BMSCs were washed twice with PBS, fixed in 4% paraformaldehyde (10 minutes) and washed again with PBS. The cells were then permeabilized with 90% ethanol (10 minutes at room temperature) and non-specific antibody binding sites were blocked with 1% normal goat serum (Vector Labs, Burlingame, Calif.) (30 minutes at room temperature). The cells were washed with PBS and incubated with either a mouse monoclonal anti-human TF IgG antibody (American Diagnostica; #4509), or, as a negative control, a mouse monoclonal IgG antibody (PharMigen, San Diego, Calif.; #03171D), at 15 µg/ml (1 hour at room temperature). Following incubation with the primary antibodies, the cells were washed 3 times with PBS and then incubated with a secondary Rhodamine Red-X conjugated goat anti-mouse IgG antibody (Molecular Probes, Eugene, Oreg.) at 10 µg/ml (45 minutes at room temperature, in the dark). Following incubation with the secondary antibodies, the cells were washed three times with PBS, and the nuclei were counter-stained blue with DAPI (Molecular Probes) at 1 ug/ml (5 minutes). Following counter-staining, the cells were washed twice with PBS, air dried, and mounted with Flouromount-G™ (Southern Biotechnology Associated Inc., Birmingham, Ala.) under a cover slip. The slides were viewed using a Leica Microstar IV phase contrast fluorescence microscope (Leica AG, Heerbrugg, Switzerland) equipped with a DAPI/FITC/Texas Red Tri colour-filter (ChromaTechnology, Brattleboro, Vt.).

All of the canine BMSCs exposed to the specific anti-TF antibody stained positively for TF, but none of the cells were stained following application of the non-specific (negative control) antibody. Thus, essentially all of the BMSCs cultured by the methods described above express TF.

Example 6

Tissue Factor Expression is also Evident in Long-Term Cultures of Canine BMSCs

While the cultures described in Examples 1–5 consist of homogeneous populations of stromal cells devoid of hematopoietic progenitor cells (Hurwitz et al., supra), BMSCs have also been classically defined as the adherent cells in long-term bone marrow cell cultures. The adherent cells support the maintenance, proliferation, and differentiation of the hematopoietic stem cells in these long-term bone marrow cultures (LTBMCs) (Dexter et al., *J. Cell. Physiol.* 91:335, 1977; Gartner and Kaplan, *Proc. Natl. Acad. Sci. USA* 77:4756, 1980).

Canine LTBMCs were established as follows. Mononuclear cells of canine bone marrow (obtained by needle stick aspiration of iliac crest of anesthetized dogs) were prepared as previously described (Hurwitz et al., supra). Mononuclear cells ($2 \times 10^7$) were suspended in 10 ml of complete medium and cultured in 25 cm$^2$ flasks at 33° C. with 5% $CO_2$. Complete medium contains MyeloCult H5100 medium (StemCell Technologies, Inc., Vancouver, Canada) supplemented with 1 µM hydrocortisone (Sigma Chemical Company), antibiotics (25 µg/ml gentamicin, 100 units/ml penicillin, 100 µg/ml streptomycin sulfate (Life Technologies, Grand Island, N.Y.)) and anti-mycotic (0.25 µg/ml amphotericin B, Life Technologies). MyeloCult H5100 medium consists of alpha-MEM, 12.5% fetal bovine serum (FBS), 12.5% horse serum, 0.2 mM i-inositol, 20 µM folic acid, 0.1 mM 2-mercaptoethanol and 2 mM L-glutamine. Cultures were fed weekly with 50% fresh medium and 50% conditioned medium. While LTBMCs consist of both adherent BMSCs and hematopoietic cells, pure cultures of stromal cells can be grown from these "mixed" LTBMCs (Chuah et al., *Human Gene Therapy* 9:353, 1998).

The cells in LTBMCs were subjected to immunofluorescence analysis using antibodies specific to TF as described in Example 5 except that the cells were permeabilized in 0.5% Triton X-100 instead of 90% ethanol, FITC-conjugated goat anti-mouse IgG antibody (Molecular Probes) was used as the secondary antibody, the nuclei were not counter-stained, and the cells were visualized with a FITC filter (ChromaTechnology).

The adherent BMSCs in the canine LTBMCs stained positively for TF following exposure to the specific anti-TF antibody, but were not stained following exposure to the non-specific (negative control) antibody.

These results demonstrate that BMSCs express TF, whether cultured within LTBMCs or as pure (homogeneous) populations of BMSCs.

Example 7

Canine BMSCs Express Active Tissue Factor when Cultured in the Same Manner as Cells Referred to as Mesenchymal Stem Cells BMSCs are also referred to as mesenchymal stem cells (or mesenchymal progenitor cells) because of their ability to differentiate into a variety of mesenchymal cell types (Prockop, *Science* 276:71, 1997). Homogenous populations of canine and human mesenchymal stem cells have been established and expanded in culture according to methods described by Kadiyala et al. (*Cell Transplant* 6:125, 1997) and Majumdar et al. (*J. Cell. Physiol* 176:57, 1998).

To demonstrate that cells grown as described in publications that make reference to "mesenchymal stem cells" (rather than BMSCs) express TF and exhibit TF procoagulant activity, the cells used in the Examples above (and referred to as BMSCs) were established in culture using the methods of Kadiyala et al., and Majumdar et al., and subjected to immunofluorescence analysis using antibodies that specifically bind to TF. The procedure was carried out as described in Example 6. The cells stained positively for TF following exposure to the specific anti-TF antibody, but were not stained following exposure to the non-specific (negative control) antibody.

The canine cells used here, whether referred to as BMSCs or mesenchymal stem cells, were established in culture as described above, harvested, and assayed for TF procoagulant activity as described in Example 4. The TF procoagulant activity was 632.7±150 ng per $10^6$ cells (average±S.D.; n=3). Thus, cells grown as described in publications that make reference to "mesenchymal stem cells" (rather than BMSCs) express TF and exhibit TF procoagulant activity.

Example 8

Tissue Factor Expression in Cultured Human BMSCs is Evident Following Immunoassay Human bone marrow was obtained by aspiration from the iliac crests of healthy volunteer donors, using local anesthetic and standard techniques. Homogenous populations of human BMSCs were cultured as previously described by Emami et al. (supra) and Hurwitz et al. (supra), and the cultured cells were subjected to immunofluorescence analysis using antibodies specific to TF, as described in Example 5.

All of the human BMSCs stained positively for TF following exposure to the specific anti-TF antibody, but none of the cells were stained following exposure to the non-specific (negative control) antibody. Thus, essentially all of the human BMSCs cultured by the methods described above express TF.

Example 9

Tissue Factor Expression is also Evident in Long-Term Cultures of Human BMSCs

Human LTBMCs were established from bone marrow aspirates from volunteer donors as described in Example 6, and the cultures were analyzed by immunofluorescence using antibodies specific to TF, as described in Example 5.

The adherent BMSCs in the human LTBMCs stained positively for TF following exposure to the specific anti-TF antibody, but were not stained following exposure to the non-specific (negative control) antibody. These results demonstrate that human BMSCs within LTBMCs express TF, as do pure populations of human stromal cells.

Example 10

Human BMSCs Express Active Tissue Factor when Cultured in the Same Manner as Cells Referred to as Mesenchymal Stem Cells As described above, BMSCs are also referred to as mesenchymal stem cells (or mesenchymal progenitor cells) (Prockop, *Science* 276:71, 1997), which have been established and expanded in culture according to methods described by Majumdar et al. (*J. Cell. Physiol.* 176:57, 1998).

To demonstrate that cells grown as described in publications that make reference to "mesenchymal stem cells" (rather than BMSCs) express TF and exhibit TF procoagulant activity, the human cells used in the Examples above (and referred to as BMSCs) were established in culture using the methods of Majumdar et al., and subjected to immunofluorescence analysis using antibodies that specifically bind to TF. The procedure was carried out as described in Example 6. The cells stained positively for TF following exposure to the specific anti-TF antibody, but were not stained following exposure to the non-specific (negative control) antibody. Thus, human cells grown as in a publication that makes reference to "mesenchymal stem cells" (rather than BMSCs) express TF.

OTHER EMBODIMENTS

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A method for reducing the risk of, or the severity of, an adverse vascular effect in a patient who is undergoing therapy comprising
 administering to the patient bone marrow stromal cells (BMSC) that have been treated ex vivo with an antisense oligonucleotide or ribozyme which inhibits expression of tissue factor (TF) or an antibody that binds to and inhibits, TF in the cells wherein said adverse vascular effect is selected from the group consisting of hemorrhage, thrombosis, and intravascular coagulation.

2. The method of claim 1, wherein the TF antagonist is an antibody.

3. The method of claim 1, wherein the TF antagonist reduces the amount of TF expressed by one or more of the cells by at least 50%.

4. The method of claim 1, wherein the TF antagonist reduces the total load of biologically active TF associated with the cells to less than about 25,000 ng/kg of the patient's weight.

5. The method of claim 1, wherein the cells comprise a DNA construct encoding Factor VIII or Factor IX.

6. The method of claim 1, wherein administration of the cells comprises injecting the cells into the patient's bloodstream or bone marrow.

7. The method of claim 1, wherein administration of the cells comprises injecting the cells into the patient's muscle tissue, an intraarticular space, dermis, or peritoneal cavity.

8. The method of claim 1, wherein the patient has hemophilia, cancer, or osteogenesis imperfecta.

9. The method of claim 1, wherein the therapy is a bone marrow transplant.

10. The method of claim 9, wherein the patient has cancer or osteogenesis imperfecta.

11. The method of claim 2, wherein the antibody is an Fab fragment.

12. The method of claim 1, further comprising administering antithrombin III to said patient.

* * * * *

SEQUENCE LISTING

<160> NUMBER OF SEQ ID NOS: 17

<210> SEQ ID NO 1
<211> LENGTH: 1866
<212> TYPE: DNA
<213> ORGANISM: Canis familiaris
<220> FEATURE:
<221> NAME/KEY: CDS
<222> LOCATION: (111)...(986)

<400> SEQUENCE: 1

```
ccgcgcccct cccgccgaca cccgctgccc cgcggcgctc cagcccgacc t ccgcaggcc     60 tcggggcgcg acgccgtcct gccagcgagc gagcgagcgc ccgccgggcc a tg aag        116
                                                        Met Lys
                                                          1 acc cgc gcc cgc ccc cgg ggg ccg cgc gcc g ag gct gcc gcc gct cgg      164
Thr Arg Ala Arg Pro Arg Gly Pro Arg Ala G lu Ala Ala Ala Ala Arg
         5                   10                  15 ctg ctc ctg ctc gcc tgg gcc ctc ctg cag g tg gcc ggg gcc tca ggc      212
Leu Leu Leu Leu Ala Trp Ala Leu Leu Gln V al Ala Gly Ala Ser Gly
     20                  25                  30 act gca gat gta gtc gta gca tat aat tta a ct tgg aaa tca act aat      260
Thr Ala Asp Val Val Val Ala Tyr Asn Leu T hr Trp Lys Ser Thr Asn
 35              40                  45                  50 ttc aag aca att ttg gag tgg gaa ccc aaa c cc atc aat cat gtc tac      308
Phe Lys Thr Ile Leu Glu Trp Glu Pro Lys P ro Ile Asn His Val Tyr
             55                  60                  65 act gtt cag ata agc cct aga cta gga aat t gg aaa agc aaa tgc ttc      356
Thr Val Gln Ile Ser Pro Arg Leu Gly Asn T rp Lys Ser Lys Cys Phe
             70                  75                  80 tac acc aca gac acg gag tgt gac ctc acc g at gaa att gtg aat gac      404
Tyr Thr Thr Asp Thr Glu Cys Asp Leu Thr A sp Glu Ile Val Asn Asp
         85                  90                  95 gtg cat cag aca tac cag gca cgg gtc ttt t cc tac cca gct gat gcc      452
Val His Gln Thr Tyr Gln Ala Arg Val Phe S er Tyr Pro Ala Asp Ala
        100                 105                 110 act gac tac tct ggg gag cct cca ttt aca a ac tcc cca gag ttc ata      500
Thr Asp Tyr Ser Gly Glu Pro Pro Phe Thr A sn Ser Pro Glu Phe Ile
115                 120                 125                 130 cct tac ata gag aca aag ctt gga cag cca a ca att cag agt ttc aaa      548
Pro Tyr Ile Glu Thr Lys Leu Gly Gln Pro T hr Ile Gln Ser Phe Lys
                135                 140                 145 caa gtt ggc aca gaa ctg aat gtg atc gta c aa gat gca cgc act ttg      596
Gln Val Gly Thr Glu Leu Asn Val Ile Val G ln Asp Ala Arg Thr Leu
                150                 155                 160 gtc aag gtg aac ggc aca ttt cta agc ctc c gg gat gtt ttc ggc aag      644
Val Lys Val Asn Gly Thr Phe Leu Ser Leu A rg Asp Val Phe Gly Lys
            165                 170                 175 gac tta agt tac aca ctt tat tac tgg aaa g ct tca agt aca gga aag      692
Asp Leu Ser Tyr Thr Leu Tyr Tyr Trp Lys A la Ser Ser Thr Gly Lys
            180                 185                 190
```

```
aaa aca gcc aag aca aac act aat gag ttt t tg att gat gtg gat gaa      740
Lys Thr Ala Lys Thr Asn Thr Asn Glu Phe L eu Ile Asp Val Asp Glu
195                 200                 205                 210 gga caa aac tac tgt ttc agt gtt caa gca g gg att cca tca cgg aaa      788
Gly Gln Asn Tyr Cys Phe Ser Val Gln Ala G ly Ile Pro Ser Arg Lys
            215                 220                 225 gct aac caa aag agt cca gaa agt ccc att g ag tgc acc agc cac gag      836
Ala Asn Gln Lys Ser Pro Glu Ser Pro Ile G lu Cys Thr Ser His Glu
        230                 235                 240 aaa ggt atg ttc aga gaa atg ttc ctc gtc a tt gga att gtg gtg ctc      884
Lys Gly Met Phe Arg Glu Met Phe Leu Val I le Gly Ile Val Val Leu
                245                 250                 255 gtg gtc atc atc ttc acc atc atc ctg tct g tg tct ctg tac aag tgc      932
Val Val Ile Ile Phe Thr Ile Ile Leu Ser V al Ser Leu Tyr Lys Cys
260                 265                 270 agg aag gtg cga gca agg caa agc ggg aag g ag agc acc cca ctc aat      980
Arg Lys Val Arg Ala Arg Gln Ser Gly Lys G lu Ser Thr Pro Leu Asn
275                 280                 285                 290 gct gca taaagaaggt gcccttggag ctgccaactg cgacaaagtt t atgttcac       1036
Ala Ala tgtgaccaag aacttttttag agaatagaat atatagaaac acaaatgagt a tttggagc   1096 ccggagacag cttgggctca cagaaagctc tttatgggac ctgttctcat g attagcatt   1156 ctggtttcgg cagcagcatt agacactttg gaatgtaatg aacgtacaac c cagtccaag   1216 tttttaaaat ttctatttta acactatggt acttttttgca cataccatgt t ttagaatgt  1276 atattctgca ccccaaatga aaccaggttg tctaatcaaa acaaatgaa c aaaaggttt   1336 aagaaatcct gggtaggtgt ttggaaaact tttgaggtga cttcaaatca t gtgggagag   1396 taaaatggaa attgggtgga ctcttctaac ataacatt gttttgtgat a tatggtatt    1456 tagcttcttc tttttttgagt tcttttggag gttcaaaaca attggcaaac t ttgaatgtg  1516 ttcaatgcag aagacttctg ttttgaggca catttcctaa agtgccttac a gtttagcac  1576 tttaactgac tcagatgctg tggattaagc acttgacagc taactctatt t ttataagac  1636 tactatacac acaccatata gaggtgatga tttacggtac tacaagcttt t atggtccat  1696 attgtatata tttatataat tttataaaag gttttatacg tggggatttt c tatttatag  1756 aagtaatatt gttctgtttg tatatattga gataatttat ttaatatact t ttatatata  1816 aataaaggtg actgggaatt gtgaaaaaaa aaaaaaaaaa aaaaaaaaaa               1866

<210> SEQ ID NO 2
<211> LENGTH: 292
<212> TYPE: PRT
<213> ORGANISM: Canis familiaris

<400> SEQUENCE: 2

Met Lys Thr Arg Ala Arg Pro Arg Gly Pro A rg Ala Glu Ala Ala Ala
1               5                   10                  15

Ala Arg Leu Leu Leu Leu Ala Trp Ala Leu L eu Gln Val Ala Gly Ala
            20                  25                  30

Ser Gly Thr Ala Asp Val Val Ala Tyr A sn Leu Thr Trp Lys Ser
        35                  40                  45

Thr Asn Phe Lys Thr Ile Leu Glu Trp Glu P ro Lys Pro Ile Asn His
    50                  55                  60

Val Tyr Thr Val Gln Ile Ser Pro Arg Leu G ly Asn Trp Lys Ser Lys
65                  70                  75                  80
```

```
Cys Phe Tyr Thr Thr Asp Thr Glu Cys Asp L eu Thr Asp Glu Ile Val
                85                  90                  95

Asn Asp Val His Gln Thr Tyr Gln Ala Arg V al Phe Ser Tyr Pro Ala
            100                 105                 110

Asp Ala Thr Asp Tyr Ser Gly Glu Pro Pro P he Thr Asn Ser Pro Glu
            115                 120                 125

Phe Ile Pro Tyr Ile Glu Thr Lys Leu Gly G ln Pro Thr Ile Gln Ser
    130                 135                 140

Phe Lys Gln Val Gly Thr Glu Leu Asn Val I le Val Gln Asp Ala Arg
145                 150                 155                 160

Thr Leu Val Lys Val Asn Gly Thr Phe Leu S er Leu Arg Asp Val Phe
                165                 170                 175

Gly Lys Asp Leu Ser Tyr Thr Leu Tyr Tyr T rp Lys Ala Ser Ser Thr
            180                 185                 190

Gly Lys Lys Thr Ala Lys Thr Asn Thr Asn G lu Phe Leu Ile Asp Val
            195                 200                 205

Asp Glu Gly Gln Asn Tyr Cys Phe Ser Val G ln Ala Gly Ile Pro Ser
    210                 215                 220

Arg Lys Ala Asn Gln Lys Ser Pro Glu Ser P ro Ile Glu Cys Thr Ser
225                 230                 235                 240

His Glu Lys Gly Met Phe Arg Glu Met Phe L eu Val Ile Gly Ile Val
                245                 250                 255

Val Leu Val Val Ile Ile Phe Thr Ile Ile L eu Ser Val Ser Leu Tyr
            260                 265                 270

Lys Cys Arg Lys Val Arg Ala Arg Gln Ser G ly Lys Glu Ser Thr Pro
        275                 280                 285

Leu Asn Ala Ala
        290

<210> SEQ ID NO 3
<211> LENGTH: 2141
<212> TYPE: DNA
<213> ORGANISM: Homo sapiens
<220> FEATURE:
<221> NAME/KEY: CDS
<222> LOCATION: (112)...(996)

<400> SEQUENCE: 3
cgggcgaacc ccctcgcact ccctctggcc ggcccagggc gccttcagcc c aacctcccc      60 agccccacgg gcgccacgga acccgctcga tctcgccgcc aactggtaga c atg gag     117
                                                         Met Glu
                                                           1 acc cct gcc tgg ccc cgg gtc ccg cgc ccc g ag acc gcc gtc gct cgg     165
Thr Pro Ala Trp Pro Arg Val Pro Arg Pro G lu Thr Ala Val Ala Arg
      5                  10                  15 acg ctc ctg ctc ggc tgg gtc ttc gcc cag g tg gcc ggc gct tca ggc     213
Thr Leu Leu Leu Gly Trp Val Phe Ala Gln V al Ala Gly Ala Ser Gly
 20                  25                  30 act aca aat act gtg gca gca tat aat tta a ct tgg aaa tca act aat     261
Thr Thr Asn Thr Val Ala Ala Tyr Asn Leu T hr Trp Lys Ser Thr Asn
 35                  40                  45                  50 ttc aag aca att ttg gag tgg gaa ccc aaa c cc gtc aat caa gtc tac     309
Phe Lys Thr Ile Leu Glu Trp Glu Pro Lys P ro Val Asn Gln Val Tyr
          55                  60                  65 act gtt caa ata agc act aag tca gga gat t gg aaa agc aaa tgc ttt     357
Thr Val Gln Ile Ser Thr Lys Ser Gly Asp T rp Lys Ser Lys Cys Phe
      70                  75                  80
```

```
tac aca aca gac aca gag tgt gac ctc acc g ac gag att gtg aag gat         405
Tyr Thr Thr Asp Thr Glu Cys Asp Leu Thr A sp Glu Ile Val Lys Asp
             85                  90                  95 gtg aag cag acg tac ttg gca cgg gtc ttc t cc tac ccg gca ggg aat         453
Val Lys Gln Thr Tyr Leu Ala Arg Val Phe S er Tyr Pro Ala Gly Asn
100                 105                 110 gtg gag agc acc ggt tct gct ggg gag cct c tg tat gag aac tcc cca         501
Val Glu Ser Thr Gly Ser Ala Gly Glu Pro L eu Tyr Glu Asn Ser Pro
115                 120                 125                 130 gag ttc aca cct tac ctg gag aca aac ctc g ga cag cca aca att cag         549
Glu Phe Thr Pro Tyr Leu Glu Thr Asn Leu G ly Gln Pro Thr Ile Gln
                135                 140                 145 agt ttt gaa cag gtg gga aca aaa gtg aat g tg acc gta gaa gat gaa         597
Ser Phe Glu Gln Val Gly Thr Lys Val Asn V al Thr Val Glu Asp Glu
            150                 155                 160 cgg act tta gtc aga agg aac aac act ttc c ta agc ctc cgg gat gtt         645
Arg Thr Leu Val Arg Arg Asn Asn Thr Phe L eu Ser Leu Arg Asp Val
            165                 170                 175 ttt ggc aag gac tta att tat aca ctt tat t at tgg aaa tct tca agt         693
Phe Gly Lys Asp Leu Ile Tyr Thr Leu Tyr T yr Trp Lys Ser Ser Ser
            180                 185                 190 tca gga aag aaa aca gcc aaa aca aac act a at gag ttt ttg att gat         741
Ser Gly Lys Lys Thr Ala Lys Thr Asn Thr A sn Glu Phe Leu Ile Asp
195                 200                 205                 210 gtg gat aaa gga gaa aac tac tgt ttc agt g tt caa gca gtg att ccc         789
Val Asp Lys Gly Glu Asn Tyr Cys Phe Ser V al Gln Ala Val Ile Pro
                215                 220                 225 tcc cga aca gtt aac cgg aag agt aca gac a gc ccg gta gag tgt atg         837
Ser Arg Thr Val Asn Arg Lys Ser Thr Asp S er Pro Val Glu Cys Met
            230                 235                 240 ggc cag gag aaa ggg gaa ttc aga gaa ata t tc tac atc att gga gct         885
Gly Gln Glu Lys Gly Glu Phe Arg Glu Ile P he Tyr Ile Ile Gly Ala
            245                 250                 255 gtg gta ttt gtg gtc atc atc ctt gtc atc a tc ctg gct ata tct cta         933
Val Val Phe Val Val Ile Ile Leu Val Ile I le Leu Ala Ile Ser Leu
            260                 265                 270 cac aag tgt aga aag gca gga gtg ggg cag a gc tgg aag gag aac tcc         981
His Lys Cys Arg Lys Ala Gly Val Gly Gln S er Trp Lys Glu Asn Ser
275                 280                 285                 290 cca ctg aat gtt tca taaaggaagc actgttggag ctactgca aa tgctatattg        1036
Pro Leu Asn Val Ser
                295 cactgtgacc gagaactttt aagaggatag aatacatgga aacgcaaatg a gtatttcgg      1096 agcatgaaga ccctggagtt caaaaaactc ttgatatgac ctgttattac c attagcatt      1156 ctggttttga catcagcatt agtcactttg aaatgtaacg aatggtacta c aaccaattc      1216 caagttttaa tttttaacac catggcacct tttgcacata acatgcttta g attatatat      1276 tccgcactta aggattaacc aggtcgtcca agcaaaaaca aatgggaaaa t gtcttaaaa      1336 aatcctgggt ggacttttga aaagcttttt tttttttttt tttttgagac g gagtcttgc      1396 tctgttgccc aggctggagt gcagtagcac gatctcggct cacttgcacc c tccgtctct      1456 cgggttcaag caattgtctg cctcagcctc ccgagtagct gggattacag g tgcgcacta      1516 ccacgccaag ctaatttttg tatttttag tagagatggg gtttcaccat c ttggccagg      1576 ctggtcttga attcctgacc tcagtgatcc acccaccttg gctcccaaa g atgctagta      1636 ttatgggcgt gaaccaccat gcccagccga aaagcttttg aggggctgac t tcaatccat      1696 gtaggaaagt aaaatggaag gaaattgggt gcatttctag gacttttcta a catatgtct      1756
```

```
ataatatagt gtttaggttc ttttttttttt caggaataca tttggaaatt c aaaacaatt   1816
gggcaaactt tgtattaatg tgttaagtgc aggagacatt ggtattctgg g cagcttcct   1876
aatatgcttt acaatctgca ctttaactga cttaagtggc attaaacatt t gagagctaa   1936
ctatatttttt ataagactac tatacaaact acagagttta tgatttaagg t acttaaagc   1996
ttctatggtt gacattgtat atataatttt ttaaaaaggt ttttctatat g gggattttc   2056
tatttatgta ggtaatattg ttctatttgt atatattgag ataatttatt t aatatactt   2116
taaataaagg tgactgggaa ttgtt                                          2141
```

<210> SEQ ID NO 4
<211> LENGTH: 295
<212> TYPE: PRT
<213> ORGANISM: Homo sapiens

<400> SEQUENCE: 4

```
Met Glu Thr Pro Ala Trp Pro Arg Val Pro A rg Pro Glu Thr Ala Val
 1               5                  10                  15

Ala Arg Thr Leu Leu Leu Gly Trp Val Phe A la Gln Val Ala Gly Ala
            20                  25                  30

Ser Gly Thr Thr Asn Thr Val Ala Ala Tyr A sn Leu Thr Trp Lys Ser
        35                  40                  45

Thr Asn Phe Lys Thr Ile Leu Glu Trp Glu P ro Lys Pro Val Asn Gln
    50                  55                  60

Val Tyr Thr Val Gln Ile Ser Thr Lys Ser G ly Asp Trp Lys Ser Lys
65                  70                  75                  80

Cys Phe Tyr Thr Thr Asp Thr Glu Cys Asp L eu Thr Asp Glu Ile Val
                85                  90                  95

Lys Asp Val Lys Gln Thr Tyr Leu Ala Arg V al Phe Ser Tyr Pro Ala
            100                 105                 110

Gly Asn Val Glu Ser Thr Gly Ser Ala Gly G lu Pro Leu Tyr Glu Asn
        115                 120                 125

Ser Pro Glu Phe Thr Pro Tyr Leu Glu Thr A sn Leu Gly Gln Pro Thr
    130                 135                 140

Ile Gln Ser Phe Glu Gln Val Gly Thr Lys V al Asn Val Thr Val Glu
145                 150                 155                 160

Asp Glu Arg Thr Leu Val Arg Arg Asn Asn T hr Phe Leu Ser Leu Arg
                165                 170                 175

Asp Val Phe Gly Lys Asp Leu Ile Tyr Thr L eu Tyr Tyr Trp Lys Ser
            180                 185                 190

Ser Ser Ser Gly Lys Lys Thr Ala Lys Thr A sn Thr Asn Glu Phe Leu
        195                 200                 205

Ile Asp Val Asp Lys Gly Glu Asn Tyr Cys P he Ser Val Gln Ala Val
    210                 215                 220

Ile Pro Ser Arg Thr Val Asn Arg Lys Ser T hr Asp Ser Pro Val Glu
225                 230                 235                 240

Cys Met Gly Gln Glu Lys Gly Glu Phe Arg G lu Ile Phe Tyr Ile Ile
                245                 250                 255

Gly Ala Val Val Phe Val Val Ile Ile Leu V al Ile Ile Leu Ala Ile
            260                 265                 270

Ser Leu His Lys Cys Arg Lys Ala Gly Val G ly Gln Ser Trp Lys Glu
        275                 280                 285

Asn Ser Pro Leu Asn Val Ser
    290                 295
```

-continued

```
<210> SEQ ID NO 5
<211> LENGTH: 15
<212> TYPE: DNA
<213> ORGANISM: Canis familiaris

<400> SEQUENCE: 5
gggtcttcat ggccc                                                    15

<210> SEQ ID NO 6
<211> LENGTH: 14
<212> TYPE: DNA
<213> ORGANISM: Canis familiaris

<400> SEQUENCE: 6
tacgactaca tctg                                                     14

<210> SEQ ID NO 7
<211> LENGTH: 14
<212> TYPE: DNA
<213> ORGANISM: Homo sapiens

<400> SEQUENCE: 7
ggtctccatg tcta                                                     14

<210> SEQ ID NO 8
<211> LENGTH: 19
<212> TYPE: DNA
<213> ORGANISM: Homo sapiens

<400> SEQUENCE: 8
aagacccagc cgagcagga                                                19

<210> SEQ ID NO 9
<211> LENGTH: 14
<212> TYPE: DNA
<213> ORGANISM: Homo sapiens

<400> SEQUENCE: 9
acagtatttg tagt                                                     14

<210> SEQ ID NO 10
<211> LENGTH: 12
<212> TYPE: PRT
<213> ORGANISM: Homo sapiens

<400> SEQUENCE: 10

Cys Val Asn Glu Asn Gly Gly Cys Glu Gln Tyr Cys
 1               5                  10

<210> SEQ ID NO 11
<211> LENGTH: 6
<212> TYPE: PRT
<213> ORGANISM: Homo sapiens
```

```
<400> SEQUENCE: 11

Ser His Leu Arg Lys Val
 1               5

<210> SEQ ID NO 12
<211> LENGTH: 6
<212> TYPE: PRT
<213> ORGANISM: Homo sapiens

<400> SEQUENCE: 12

Asp His Thr Leu Ile Arg
 1               5

<210> SEQ ID NO 13
<211> LENGTH: 4
<212> TYPE: PRT
<213> ORGANISM: Homo sapiens

<400> SEQUENCE: 13

Arg Gly Asp Ser
 1

<210> SEQ ID NO 14
<211> LENGTH: 23
<212> TYPE: DNA
<213> ORGANISM: Homo sapiens

<400> SEQUENCE: 14
atttcaagac aattttggag tgg                                              23

<210> SEQ ID NO 15
<211> LENGTH: 22
<212> TYPE: DNA
<213> ORGANISM: Homo sapiens

<400> SEQUENCE: 15
agttttctcc tttatccaca tc                                               22

<210> SEQ ID NO 16
<211> LENGTH: 19
<212> TYPE: DNA
<213> ORGANISM: Canis familiaris

<400> SEQUENCE: 16
atcttgtacg atcacattc                                                   19

<210> SEQ ID NO 17
<211> LENGTH: 23
<212> TYPE: DNA
<213> ORGANISM: Canis familiaris

<400> SEQUENCE: 17
atttcaagac aattttggag tgg                                              23
```